US009633540B1

United States Patent
Teshome et al.

(10) Patent No.: US 9,633,540 B1
(45) Date of Patent: Apr. 25, 2017

(54) DEFECATION ALERT SYSTEM AND RELATED CONTROL SYSTEM AND PROCESS

(71) Applicants: Dagnachew Teshome, Los Angeles, CA (US); Joshua Dagnachew, Los Angeles, CA (US); Menelik Dagnachew, Los Angeles, CA (US); Ariam Dagnachew, Los Angeles, CA (US)

(72) Inventors: Dagnachew Teshome, Los Angeles, CA (US); Joshua Dagnachew, Los Angeles, CA (US); Menelik Dagnachew, Los Angeles, CA (US); Ariam Dagnachew, Los Angeles, CA (US)

( * ) Notice: Subject to any disclaimer, the term of this patent is extended or adjusted under 35 U.S.C. 154(b) by 0 days.

(21) Appl. No.: 15/230,265

(22) Filed: Aug. 5, 2016

(51) Int. Cl.
| | |
|---|---|
| *G08B 23/00* | (2006.01) |
| *G08B 21/18* | (2006.01) |
| *A01K 15/02* | (2006.01) |
| *A01K 27/00* | (2006.01) |
| *A01K 5/02* | (2006.01) |
| *A01K 7/02* | (2006.01) |
| *A01K 29/00* | (2006.01) |
| *A01K 1/01* | (2006.01) |
| *A01K 1/015* | (2006.01) |

(Continued)

(52) U.S. Cl.
CPC ............ *G08B 21/18* (2013.01); *A01K 1/0107* (2013.01); *A01K 1/0157* (2013.01); *A01K 5/02* (2013.01); *A01K 7/02* (2013.01); *A01K 11/007* (2013.01); *A01K 15/023* (2013.01); *A01K 15/029* (2013.01); *A01K 27/009* (2013.01); *A01K 29/005* (2013.01); *A61B 5/073* (2013.01)

(58) Field of Classification Search
CPC ... A61B 5/4255; A61B 10/0038; A61B 5/073; G06F 19/3418; G08B 21/0453; G08B 21/0484; G08B 21/0211; G08B 21/18; A01K 1/0107; A01K 1/0157; A01K 15/023; A01K 15/029; A01K 27/009; A01K 5/02; A01K 7/02; A01K 29/005; A01K 11/007
USPC ................ 340/573.1, 573.5, 539.11, 539.12; 600/300, 304, 587, 593; 128/903
See application file for complete search history.

(56) References Cited

U.S. PATENT DOCUMENTS

| | | |
|---|---|---|
| 7,427,266 B2 | 9/2008 | Ayer |
| 7,796,043 B2 | 9/2010 | Euliano |
| 8,514,067 B2 | 8/2013 | Hyde |

(Continued)

FOREIGN PATENT DOCUMENTS

WO    WO 2016065082 A1 *   4/2016   ........... A61B 5/4255

*Primary Examiner* — Thomas Mullen
(74) *Attorney, Agent, or Firm* — Lowry Blixseth LLP; Scott M. Lowry

(57) ABSTRACT

The defecation control system process disclosed herein includes activating a communication circuit of at least one ingestible tracker having a size and shape for travel to a rectum of a host and a transmission circuit of a monitor fixable to the host at a substantially constant distance relative to the rectum, generating at least one tracking distance based at least in part on communication between the communication circuit of the ingestible tracker and the transmission circuit of the monitor, comparing the tracking distance to a predetermined trigger distance stored in a database, and activating an electronic accessory when the tracking distance is within a predetermined threshold of the trigger distance.

30 Claims, 15 Drawing Sheets

(51) Int. Cl.
*A01K 11/00* (2006.01)
*A61B 5/07* (2006.01)

(56) References Cited

U.S. PATENT DOCUMENTS

| | | |
|---|---|---|
| 8,947,240 B2 | 2/2015 | Mainini |
| 9,183,724 B2 | 11/2015 | Covannon |
| 2005/0192489 A1 | 9/2005 | Marshall |
| 2008/0001735 A1* | 1/2008 | Tran .................... G06F 19/3418 340/539.22 |
| 2008/0252464 A1 | 10/2008 | Panasevich |
| 2009/0124871 A1 | 5/2009 | Arshak |
| 2011/0080291 A1* | 4/2011 | Ishimoto ............ G08B 21/0484 340/573.1 |
| 2014/0276218 A1* | 9/2014 | Hyde ................. A61B 10/0038 600/575 |
| 2016/0044897 A1 | 2/2016 | Waymouth |

* cited by examiner

DEFECATION ALERT SYSTEM AND RELATED CONTROL SYSTEM AND PROCESS

BACKGROUND OF THE INVENTION

The present invention generally relates to a defecation alert system and related control system and process related to the same. More specifically, the present invention relates to a defecation alert system that identifies when an ingestible tracker is at or near the rectum of a host thereby identifying an impending defecation, and the related control system and process may operate certain electronic accessories interactive with the host prior to or after the defecation.

In general, the prior art discloses ingestible RFID devices that can be tracked through the digestive tract of a host (e.g., an animal or human). The ingested RFID tag may transmit real-time location information to a remote monitor, such that the monitor may alert the host or a third party that the RFID tag has reached a particular location within the host (e.g., the digestive tract). Although, the problem is that there are no known prior art ingestible RFID devices that communicate information related to when the host (e.g., an animal or human) needs to defecate, or that the host requires food, water, or other types of assistance (such as with an infant or elderly person in an assisted living environment).

For example, an animal such as a dog typically requires assistance from a caretaker to ensure the dog is able to go outside to go to the bathroom, and to ensure the dog receives more food and/or water when needed. Owners can typically learn the behavior of their pet over time, based on behavior habits and food consumption. But, learning these behaviors requires an attentive owner and can take a lot of time. Even so, there is still a certain amount of guesswork involved because the owner really never knows exactly when the pet needs to go to the bathroom, or requires more food and/or water. Moreover in this respect, the process for training the dog to identify certain permissible areas to defecate can take time. As such, knowing when the dog is about to defecate can greatly improve the efficiency of training the dog to defecate in certain locations at specific times. This can be reinforced with positive stimuli such as dropping a dog treat from a dispenser or issuing an audible praise in the voice of the owner from a speaker attached to the dog collar. At a minimum, knowing the approximate time a dog needs to defecate enhances remote monitoring and care, and may provide some level of notification that the dog/pet needs more water and/or food.

In another example, untrained infants also require close supervision from a parent for purposes of helping the infant identify the need to defecate, and the proper location for defecating. Again, even with attentive parents who learn the behavior of the infant over time, there may be a significant amount of guesswork in identifying when the infant needs to defecate. As such, in some cases, it can take years to train an infant to defecate in the proper location. Although, if the parent has some idea when the infant needs to defecate, the parent can better help the infant identify or associate the need to defecate with using the bathroom (as opposed to a diaper). Through time, this can help train the infant more quickly. Similarly, third party caretakers for older persons unable to control their bowel movements may simply schedule periodic visits to attend to the defecation needs. For example, in a hospital or assisted living environment, the third party caretaker may simply set a schedule to periodically visit patients. Those visits may require changing incontinence products in the event the patient does not or is otherwise unable to make it to the bathroom before defecating. In this respect, it is preferable that the third party caretaker arrive some time before the patient defecates, so the caretaker can help the patient to the bathroom, instead of using the incontinence product. Again, knowing when the patient is about to defecate allows the third party caretaker to better allocate resources and assist patients when they actually need help (as opposed to a guesswork schedule).

The prior art discloses systems and devices that monitor the internal biological conditions of a person or animal by ingesting a tracking sensor. The animal or human basically ingests a biologically-inert sensor that can travel through the gastrointestinal ("GI") tract. The sensor may record data when passing through the GI tract and, optionally, wirelessly transmit data in real-time to an external controller that monitors and/or processes the data. Some prior art sensors are recoverable, e.g., by way of a bowel movement, to subsequently retrieve the data therefrom. Although, such ingestible sensors known in the art only monitor conditions that relate to internal biological conditions (e.g., temperature) for purposes of verifying the health of the GI tract. Such prior art sensors cannot and do not otherwise determine the approximate time the host (e.g., animal or person) needs to defecate.

In one prior art example, U.S. Publication No. 2005/0192489 to Marshall, the contents of which are herein incorporated by reference in its entirety, discloses an ingestible data recorder designed to pass through the body, while communicating with a wireless monitoring device via a radiofrequency communications interface. The capsule data recorder can sense and record data regarding biological conditions in the digestive tract as the capsule sensor travels therethrough. When the capsule senses a particular feature or environmental factor within the digestive tract, such as a cancer cell, the capsule wirelessly notifies the monitoring device of its location within the host. Importantly, a triggering biological constituent is required before the ingestible device begins data transmission. This can help pinpoint and diagnose certain medical conditions, such as cancer, but such a device certainly does not provide external notification regarding an impending bowel movement. In fact, the Marshall ingestible data recorder does not even continuously transmit its location or surrounding conditions to a monitor.

In another example, U.S. Pat. Nos. 8,514,067 and 8,599,067, both to Hyde, the contents of which are herein incorporated by reference in their entireties, each disclose an ingestible RFID tag designed for wireless detection in a toilet bowl by an attached monitoring unit after passing from the host during a bowel movement. Each Hyde reference also discloses a system wherein a handheld device can be used to interrogate an implanted sensor in a particular region of interest in the host. The capsule actively emits a signal readable by the handheld device for purposes of determining the location of the sensor. Although, the Hyde references do not provide advanced notification of a potential bowel movement. Rather, the system is only able to identify when the ingestible capsule is in the toilet bowl, which is too late in terms of providing advanced notification regarding the need to defecate.

In another prior art reference, U.S. Pat. No. 7,427,266 to Ayer, the contents of which are herein incorporated by reference in its entirety, discloses an ingestible RFID tag in pill form used in conjunction with a wearable or implantable sensor used to receive wireless signals from the RFID tag to monitor whether the RFID tag was ingested by a host (e.g., a human or animal). Ayer also discloses that the RFID tag may include a dissolvable coating that can result in a change in RFID tag output once removed, thereby allowing for variable transmissions to the corresponding sensor. Although, Ayer does not track the location of the RFID tag, such that the coupled sensor can detect and issue an alert when the RFID tag has entered a particular part of the host digestive track (e.g., at about the time of defecation). Rather, Ayer discloses notifications from the sensor based only on whether the RFID tag was ingested by the host.

Furthermore, U.S. Pat. No. 7,796,043 to Euliano, the contents of which are herein incorporated by reference, discloses an ingestible electronic pill detectable in a host GI tract by an external monitor. Ingestion of the electronic pill, and its detection generally within the GI tract, prompts a notice to care providers that the host ingested the pill. Euliano does not disclose the continued monitoring of that pill throughout the GI tract. Euliano only confirms ingestion generally, and fails to provide any notice that the host needs to defecate.

U.S. Publication No. 2009/0124871 to Arshak discloses an ingestible capsule with an acoustic transducer that may be monitored in real-time via a fixed external acoustic emitter and receiver as the capsule passes through the GI tract. In essence, Arshak discloses an echo-location tracker in the form of an ingestible pill that includes a plurality of sensors that can transmit data via radiofrequencies. Although, Arshak does not disclose delivery of external monitoring notifications once the RFID tag reaches a particular location within the host gastrointestinal tract.

Finally, U.S. Pat. No. 9,183,724 to Covannon, the contents of which are herein incorporated by reference in its entirety, discloses a system for tracking the ingestion of medicines through the use of RFID tags that begin transmitting only upon digestion within the GI tract. The Covannon system also optionally includes the activation of remote mechanical and electrical mechanisms upon notification of tracker ingestion, such as electronic door locks, but only in response to digestion of the RFID tags. Covannon also fails to disclose sending notifications (or activating anything for that matter) in response to an impending defecation, e.g., based on the location of the ingestible tag within the GI tract (e.g., at or near the rectum).

There exists, therefore, a significant need in the art for a defecation alert system and related control system and process related to the same that includes an ingestible tracker that wirelessly communicates with a controller for providing an external notification that the host is about to defecate, and further wherein the host may require assistance with respect to the timing and location of the defecation, obtaining additional food or water, etc. The present invention fulfills these needs and provides further related advantages.

SUMMARY OF THE INVENTION

The defecation control system process as disclosed herein generally includes activating a communication circuit of at least one ingestible tracker having a size and shape for ingestion and travel to a rectum of a host and a transmission circuit of a monitor fixable to the host at a substantially constant distance relative to the rectum. Next, at least one tracking distance is generated and may be based at least in part on communication between the communication circuit of the ingestible tracker and the transmission circuit of the monitor. In this respect, the tracking distance may be calculated based on the positioning of the ingestible tracker relative to the monitor. The tracking distance is then compared to a predetermined trigger distance (e.g., based on triangulation, signal strength, etc.) stored in a database and an electronic accessory is operated when the tracking distance is within a predetermined threshold of the trigger distance, which indicates that the host needs to defecate.

With respect to the electronic accessories, in one embodiment, the electronic accessory may include a camera whereby the operating step includes recording at least one picture of the host with the camera and relaying the at least one picture for remote viewing. In another embodiment, the electronic accessory may include a door lock and the operating step may include unlocking a door. Alternatively, the operating step may include energizing an electronic fence designed to create a path to lead the host to a designated defecation area. In this embodiment, the electronic fence may be operable with a wearable shock collar that help guides the host (e.g., a dog). In another embodiment, the electronic accessory may include a toilet and the operating step may include actuating a flush valve of the toilet. In another embodiment, the electronic accessory may include an audio system and the operating step may include initiating an audible alarm. The electronic accessory may also include a lighting system that may illuminate a path to a bathroom, illuminate a defecation area, illuminate a defecation mat, etc. upon sensed notification that the host needs to defecate. In another alternative embodiment, the electronic accessory may include a networked computer that receives an issued alert from a controller.

Furthermore, the activating step may include the step of activating the communication circuit of the ingestible tracker after dissolving at least part of a housing of the ingestible tracker to expose a sensor. The generating step may also include generating multiple tracking distances for real-time comparison to the predetermined trigger distance and the operating step may include changing the electronic accessory from a first non-use state to a second use state, and issuing an operation notification when the electronic accessory is in the second use state. Here, the changing step may also include changing the electronic accessory back from the second use state to the first non-use state and issuing a completion notification.

In another aspect, the process disclosed herein may include sensing removal of the ingestible tracker from the host and issuing a removal notification. Further in this respect, the process may include dispensing consumables such as dog food or water in response to sensed removal of the ingestible tracker from the host. Additionally, the system may simultaneously track the location of multiple ingestible trackers, wherein each of the multiple ingestible trackers has a unique and varying real-time tracking distance. Accordingly, these unique and varying real-time tracking distances may simultaneously be compared with respective unique and predetermined trigger distances to determine whether one or more of the hosts carrying the ingestible trackers needs to defecate. The generating step may also include a transmission circuit that sends a transmission query to a passive RFID circuit communication circuit. The transmission query may energize the RFID circuit such that the RFID circuit can provide a response.

A defecation alert system as disclosed herein may include an ingestible tracker having a size and shape for ingestion and travel to a rectum of a host. Similarly, the ingestible tracker may have a communication circuit for unilateral or bilateral wireless communication. A monitor fixable to the host at a substantially constant distance relative to the rectum (e.g., by way of a clip that attaches to an article of clothing) may also have a transmission circuit for communication with the communication circuit of the ingestible tracker. Of course, the monitor could also include multiple monitors positioned at different locations. Here, communication between the communication circuit and the transmission circuit may establish at least one tracking distance related to the distance the ingestible tracker is from the rectum of the host. The system may also include a controller having a network adapter that can communicate with the monitor and/or the ingestible tracker to at least receive the tracking distance for comparison to a trigger distance stored in a database. The controller may use the comparison to determine when the tracking distance is within a predetermined threshold of the trigger distance to identify when the host needs to defecate. Furthermore, such a system may include an electronic accessory configured to at least receive operational instructions from the controller. Here, the controller can issue at least one operational instruction to change the electronic accessory from a first non-use state before the controller identifies that the host needs to defecate to a second use state after the controller identifies that the host needs to defecate.

In another aspect of the system disclosed herein, the communication circuit may include an RFID chip (e.g., a passive RFID circuit) or a Bluetooth transmitter. In the embodiment where the communication circuit is an RFID circuit, the transmission circuit may include a reader for proactively querying and energizing the passive RFID circuit so the ingestible tracker may provide a response (e.g., tracking information). Further in this respect, the communication circuit, the transmission circuit, and the network adapter may all communicate wirelessly.

The ingestible tracker may include an outer casing hermetically sealing the communication circuit therein. Additionally or alternatively, at least a portion of the outer casing may include a dissolvable housing that exposes at least one sensor once dissolved. Here, the communication circuit may remain hermetically sealed within the outer casing after the dissolvable housing dissolves and the sensor becomes exposed. This allows the sensor to sense certain biological conditions within the body while shielding the communication circuit within the outer casing. In this respect, the outer casing may be made from metal, ceramic, or a polymer material.

The electronic accessory may include a variety of electronically operable devices that include a video system, an electronic door lock, an electronic pathway, a training collar, an electrically-actuating toilet valve, a siren, a lighting system, an audio replay system, or a food dispenser. In another example, the electronic accessory may include a networked computer and the second use state may include an alert, such as an audible or visual alert presented on a cell phone, a desktop computer, a laptop, or a tablet.

In another embodiment, the defecation control system process may include steps for activating a communication circuit of an ingestible tracker having a size and shape for ingestion and travel to a rectum of a host; capturing at least one image within a tractus digestorius of the host with a camera associated with the ingestible tracker; analyzing the at least one image for a set of biological characteristics; comparing the set of biological characteristics to a set of trigger characteristics; and operating an electronic accessory when the set of biological characteristics are within a predetermined percentage of the set of trigger characteristics indicating the ingestible tracker is in a location at or near the rectum such that the host needs to defecate.

In one aspect of this embodiment, the operating step may include the step of energizing an electronic accessory that includes an electronic fence leading the host to a designated defecation area and operable with a wearable shock collar. In another embodiment, the electronic accessory may include a toilet and the operating step may include the step of actuating a flush valve. Alternatively, the activating step may include the step of activating the communication circuit of the ingestible tracker after dissolving at least part of a housing of the ingestible tracker to expose the camera. In another embodiment, the electronic accessory may include a lighting system and the operating step may include illuminating a path to a bathroom. Additionally, the processes disclosed herein may include the step of sensing removal of the ingestible tracker from the host and issuing a removal notification and/or include the step of dispensing consumables, such as dog food, in response to sensed removal of the ingestible tracker from the host.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
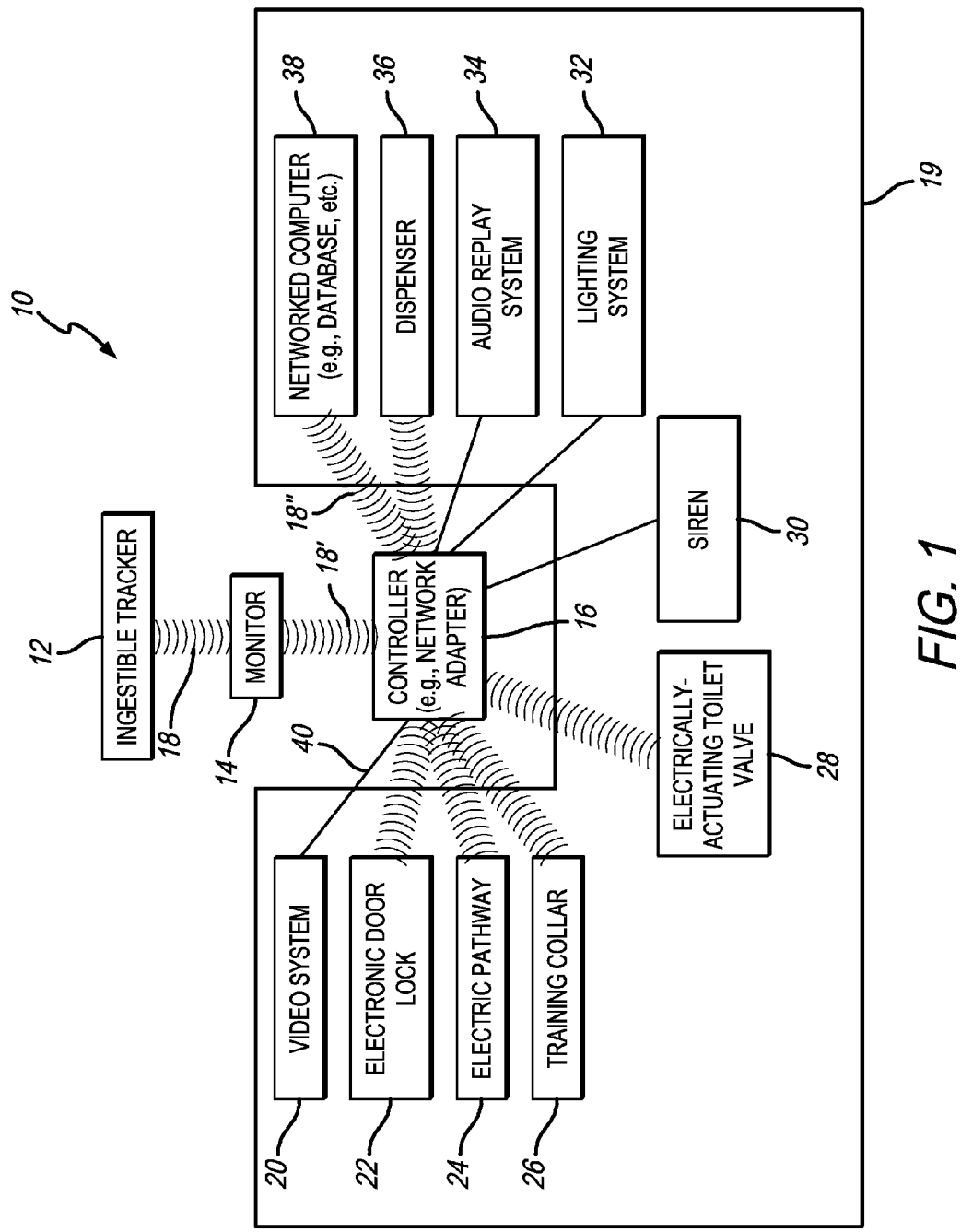
FIG. 1 is a diagrammatic view of a defecation alert system and related control system as disclosed herein, generally illustrating wireless communication among an ingestible tracker, a monitor for generally identifying the location of the ingestible tracker, and a controller for coordinating operation of the system, such as by way of wireless or hardwire communication with one or more optional electronic accessories.

As shown in the exemplary drawings for purposes of illustration, the present invention for a defecation alert system is generally referred to by reference numeral 10 in FIG. 1, and the related control system and process are shown with respect to the flow charts and diagrams in FIGS. 5-13C. As shown in FIG. 1, the defecation alert system 10 may include an ingestible tracker 12 (e.g., including, but not limited to, an RFID chip, Bluetooth transmitter, wireless transmitter, or non-wireless tracking pill), a monitor 14 for communicating with the ingestible tracker 12, and a central controller 16 for operating the system 10. In various embodiments, the monitor 14 and the controller 16 may be integrated as one device, or the monitor 14 may simply operate as both a monitor and a controller, and vice versa. In FIG. 1, the ingestible tracker 12 is shown conveying information to the monitor 14 via a wireless signal 18. Similarly, the monitor 14 may transmit information (e.g., the same or different information received from the ingestible tracker 12) via a wireless signal 18' to the controller 16. Alternatively, the ingestible tracker 12 may communicate directly with the controller 16. Moreover, the monitor 14 and/or the controller 16 may communicate with one or more of a variety of electronic accessories 19 to operate the defecation alert system 10 as disclosed herein. For example, the electronic accessories 19 may include, but are not necessarily limited to, one or more of a combination of a video system 20, an electronic door lock 22, an electric pathway 24 (e.g., an electronic fence), a training collar 26, an electrically-actuating toilet valve 28, a siren 30, a lighting system 32, an audio replay system 34, a dispenser 36, and/or a networked computer 38. For example, the audio replay system 34 may provide positive audible feedback (e.g., "STOP", "Good Boy!", etc.) to a baby or a dog (e.g., if attached to a dog collar), after the baby or dog defecates in a desired location. The electronic accessory 19 may also include an electronic mat identifying an area designated as the proper place for defecation. Although, of course, a person of ordinary skill in the art may recognize that other electronic accessories may be compatible for use with the system 10 disclosed herein. Such electronic accessories could include more than those identified with respect to the electronic accessories 19, as these are just exemplary electronic accessories compatible with the system 10. As such, this list is non-exhaustive.

In one embodiment, the controller 16 may be the central information and control hub for the system 10. In this respect, the controller 16 may communicate with one or more of the electronic accessories 19 by way of a wireless signal (e.g., such as a Wi-Fi signal 18" shown in FIG. 1 communicating with the networked computer 38) or by way of a hardwire connection (e.g., such as an Ethernet connection 40 shown in FIG. 1 communicating with the video system 20). Of course, the controller 16 may communicate with one or more of the electronic accessories 19, or other electronic accessories as needed and/or desired, by way of wireless communication network(s) (e.g., Wi-Fi, NFC, cellular networks such as 3G or 4G LTE, Bluetooth, Bluetooth low energy (BLE), etc.) and/or hardwire communication network(s) (e.g., Ethernet, cable internet, DSL, etc.). The hardwire communication network(s) may be used in higher security applications to prevent wireless data signal interception.

Figure 2:
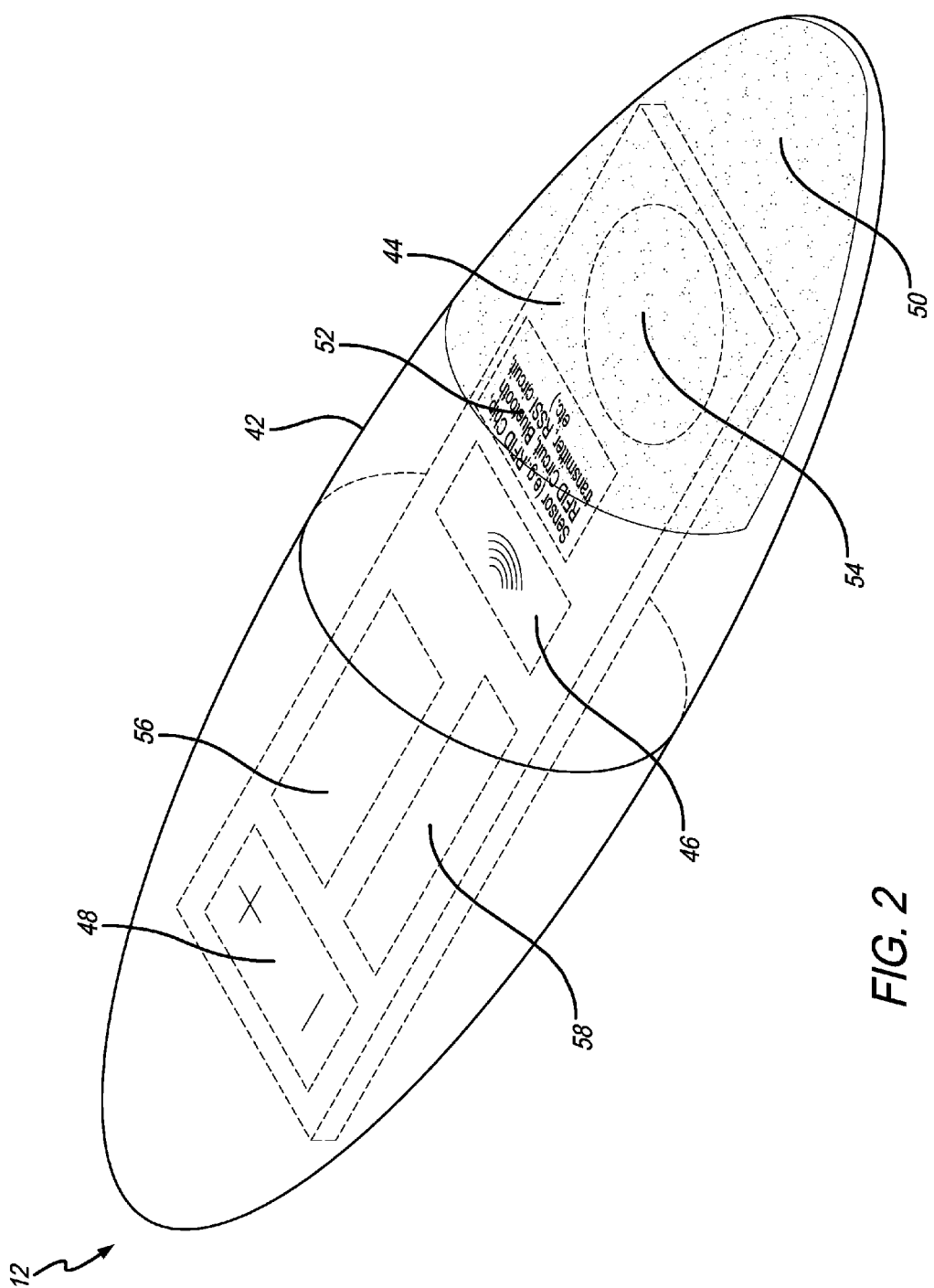
FIG. 2 is a perspective view of the ingestible tracker, including a circuit board encapsulated by a protective casing.

FIG. 2 is a perspective view illustrating one embodiment of the ingestible tracker 12, including an outer casing 42 generally encompassing and hermetically sealing a circuit board 44 therein. Such a fluid-resistant outer casing 42 is shown in FIG. 2 in the general shape of a hollow pill-shaped nonconductive enclosure where the internal circuitry coupled to the circuit board 44 remains secured and electrically isolated therein. Sealing the circuit board 44 therein prevents exposure of any conductive electrical connections with the surrounding environment (e.g., bodily fluids), thus preventing short circuits or unwanted discharges. The outer casing 42 may be constructed of a durable biologically inert material such as metal, ceramic, a polymer, or a combination of one or more of these or other such biologically inert materials. The outer casing 42 may be opaque to conceal the components therein, may be transparent for viewing the internal circuitry, or may be a combination wherein part of the outer casing 42 is transparent and another part of the outer casing 42 is opaque. In one embodiment, all or a portion of the outer casing 42 may include externally viewable indicia, such as a logo.

More specifically, the circuit board 44 within the outer casing 42 may include at least a wireless transmitter 46, such as an RFID transmitter, Bluetooth transmitter, or the like. In one embodiment, the circuit board 44 may be unpowered and include a passive RFID transmitter. Here, an in-range reader may emit a signal querying the status and/or location of the ingestible tracker 12. The signal from the reader may be used to energize the RFID transmitter so the ingestible tracker 12 can generate and emit a response signal for reception by the reader, for eventual transmission to the controller 16. The response signal may include a variety of information, including the location of the ingestible tracker 12. In another embodiment, the circuit board 44 may further include a power source 48 for powering the wireless transmitter 46 and/or other components of the circuit board 44. In this embodiment, the power source 48 may be used in association with an active wireless transmitter, i.e., a transmitter that generates and emits its own signal and/or information, and is not otherwise reliant on an external reader to provide an energizing signal.

In general, the circuit board 44 may be a printed circuit board with the wireless transmitter 46 and/or the power source 48 being conductively soldered or adhered thereto. The circuit board 44 may be sheltered from fluid contact by way of the hermetically enclosed outer casing 42, as briefly mentioned above. Although, in an alternative embodiment, a portion of the outer casing 42 may include a dissolvable housing 50 that dissolves in certain biological environments (e.g., in the stomach or other part of the digestive tract) to expose certain circuitry therein. Furthermore, such a dissolvable housing 50 may dissolve after a predetermined duration, similar to a time release capsule or pill. Once the housing 50 is dissolved, certain circuitry inside the ingestible tracker 12 may be exposed, such as a sensor 52 and/or a camera 54. In this configuration, the outer casing 42 may continue to shelter sensitive electronics, such as the circuit board 44, the wireless transmitter 46, the battery or power source 48, a processor 56, and/or a-storage media 58, to prevent exposure of electrical interconnections to conductive elements in the surrounding environment (e.g., bodily fluids). When exposed, the sensor 52 may detect a variety of bodily conditions such as temperature, pressure, pH level, salinity, cytotoxicity, or the like. The sensor 52 may also be used to determine relative positioning of the ingestible tracker 12, such as by way of triangulation, GPS location and/or received signal strength indication (RSSI). Persons of ordinary skill in the art will readily recognize that the sensor 52 may include a single sensor integrated with the circuit board 44, or the sensor 52 may include a plurality of sensors integrated with the circuit board 44 or otherwise combined together in a single interchangeable unit.

Additionally, in an alternative embodiment, the camera 54 may allow the tracker 12 to operate independently of the monitor 14 and/or the controller 16. In this embodiment, the camera 54 may record infrared and/or visible-light imagery, and may incorporate a selectively-activated light source that assists in image recording. The camera 54 may work with or without the dissolvable housing 50. In the embodiment where the ingestible tracker 12 does not include the dissolvable housing 50, the outer casing 42 may be transparent to better ensure the clarity of the pictures. In this respect, the camera 54 may periodically capture images as the ingestible tracker 12 travels through the Tractus digestorius. The characteristics of the images are then compared (e.g., by optical image recognition) to sample or stock images usable as a point of comparison to determine the location of the ingestible tracker 12 within the Tractus digestorius. For example, the camera 54 may initially capture images of the body tissue lining the esophagus, which indicates that the ingestible tracker 12 is being swallowed. Subsequent images may identify internal body tissue that represents the stomach 73 or the intestines 74. Accordingly, images captured by the camera 54 that closely match the internal body tissue of the rectum 76 (or otherwise show a sufficient amount of fecal matter) may indicate that the ingestible tracker 12 has reached the rectum 76. The images may be processed locally by the processor 56, or the images may be transmitted to the monitor 14 and/or the controller 16 for external processing. In the embodiment where the images are processed locally by the processor 56, the ingestible tracker 12 may communicate directly with one or more of the electronic accessories 19 by way of the wireless transmitter 46, to operate those one or more electronic accessories 19 as disclosed herein, when the processor 56 determines that the ingestible tracker 12 is at or near the rectum 76.

Alternatively, the processor 56 may receive and process data from one or more of the sensors 52 and/or the camera 54 for real-time remote transmission by way of the wireless transmitter 46. Here, image processing may occur remotely by the monitor 14 and/or the controller 16. In another alternative embodiment, the storage media 58 may store raw data, processed data, or other information from one or more of the sensors 52 and/or the camera 54 for later transmission and/or retrieval, such as for external processing.

In one embodiment, the wireless transmitter 46 may start transmitting data before the host swallows the ingestible tracker 12. This way, the system 10 can track location information of the ingestible tracker 12 from initial ingestion until defecation or the like, and may provide enhanced location results. Alternatively, the wireless transmitter 46 may begin transmitting in response to the sensor 52 activating after the housing 50 dissolves. Here, one or more of the sensors 52 may initiate upon sensing certain biological conditions, such as bodily fluids. In other words, the ingestible tracker 12 may automatically activate upon ingestion or the ingestible tracker 12 may activate when triggered by an external stimuli at some point after ingestion. Delaying activation may conserve energy, thereby increasing the usable life of the power source 48.

Figure 3:
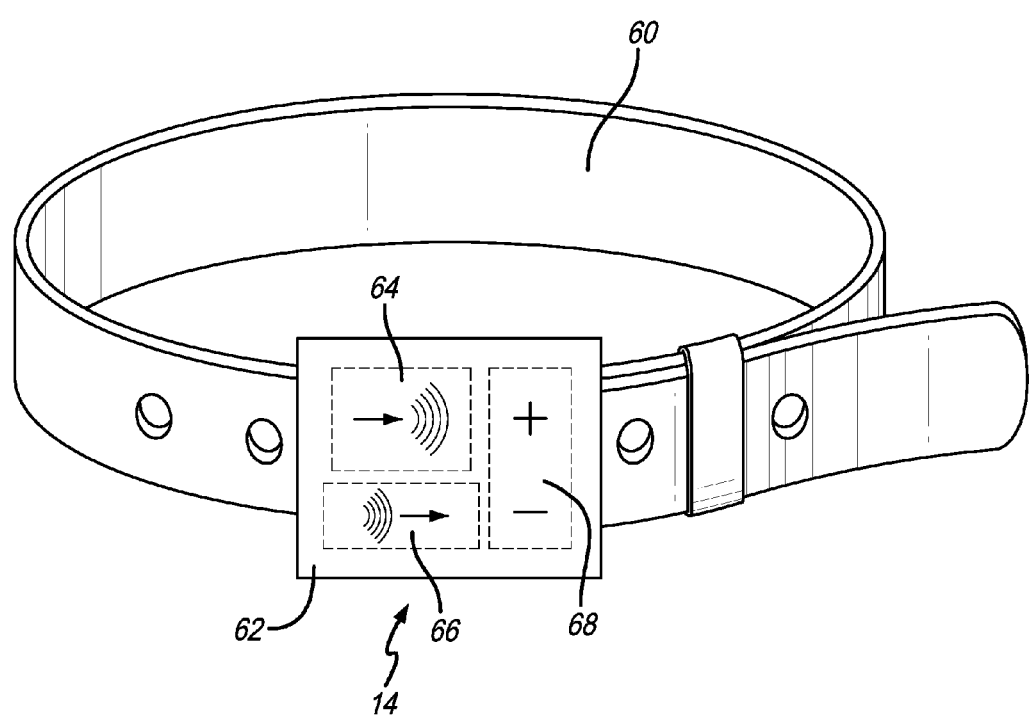
FIG. 3 is a perspective view of a monitor mounted to an adjustable belt.

FIG. 3 is a perspective view of one embodiment of the monitor 14 as coupled to a belt 60. The monitor 14 may include a housing 62 generally protecting a wireless receiver 64, a wireless signal transmitter 66, and/or a battery 68. The wireless receiver 64 may be configured to selectively receive location information and/or sensory data (as applicable) from the wireless transmitter 46 within the ingestible tracker 12. Further in this respect, the wireless signal transmitter 66 as part of the monitor 14 may wirelessly send information received from the ingestible tracker 12 to the controller 16, which may be positioned at some remote location, such as a server room or the like. The controller 16 may then process the location information and/or sensory data (as applicable) in real-time or at periodic intervals, depending on the transmission frequency. The battery 68 provides electrical power for the monitor 14, thus providing the convenience of cordless portability. The battery 68 may be a non-removable or removable rechargeable battery. In the embodiment wherein the battery 68 is non-removable, the battery 68 may otherwise be inaccessible within the housing 62. Alternatively, the battery 68 may be a non-rechargeable battery that requires periodic removal and replacement. In this embodiment, the battery 68 may be accessed by way of an externally accessible access panel (not shown) built into the housing 62. While the monitor 14 is shown with respect to FIG. 3 as being attached to the belt 60, the monitor 14 may also couple to another clothing garment (e.g., strap, pants, shirt, collar in the case of a pet, etc.).

Figure 4:
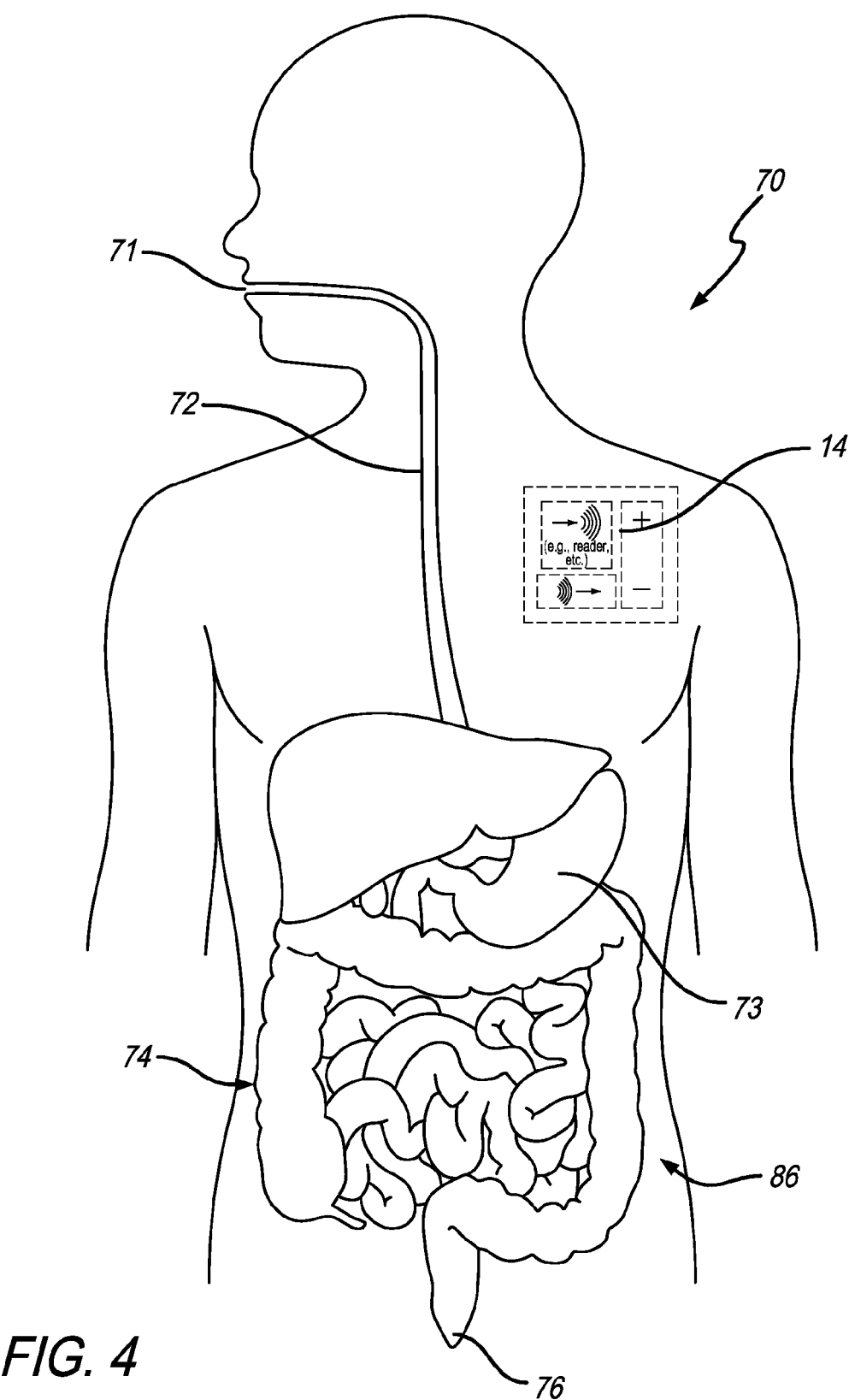
FIG. 4 is a diagrammatic view of a human host having the monitor implanted therein at a static position relative to a rectum.

FIG. 4 is a diagrammatic view of a human host 70 generally having an open mouth 71 that provides passage for food and other consumables to an esophagus 72 coupled to a stomach 73 for digestion. The stomach 73 then passes food and other consumables to the intestines 74 for further digestion, which terminate at a rectum 76. In the embodiment shown with respect to FIG. 4, the monitor 14 may be implanted within the human host 70 to relatively substantially statically position the wireless receiver 64 in a fixed position while receiving wireless signals from the ingestible tracker 12. FIG. 4 illustrates the tracker 14 implanted above the pectoral muscle, but the monitor 14 could also be implanted closer to the rectum 76. In this embodiment, the monitor 14 may be shielded or focused on a particular location or zone within the human host 70, such as the rectum 76. As such, the monitor 14 will only identify when the tracker 12 is at or near the rectum 76 (e.g., similar to a proximity sensor). In these embodiments, the housing 62 must be hermetically sealed and constructed from a durable biologically inert material. The monitor 14 may also be relatively statically positioned by attaching the monitor 14 to an article of clothing, such as the belt 60 shown in FIG. 3. Ensuring the monitor 14 remains in a substantially fixed position may help ensure the accuracy of determining the location of the ingestible tracker 12 before defecation, and especially when the ingestible tracker 12 is located at or near the rectum 76.

Figure 5:
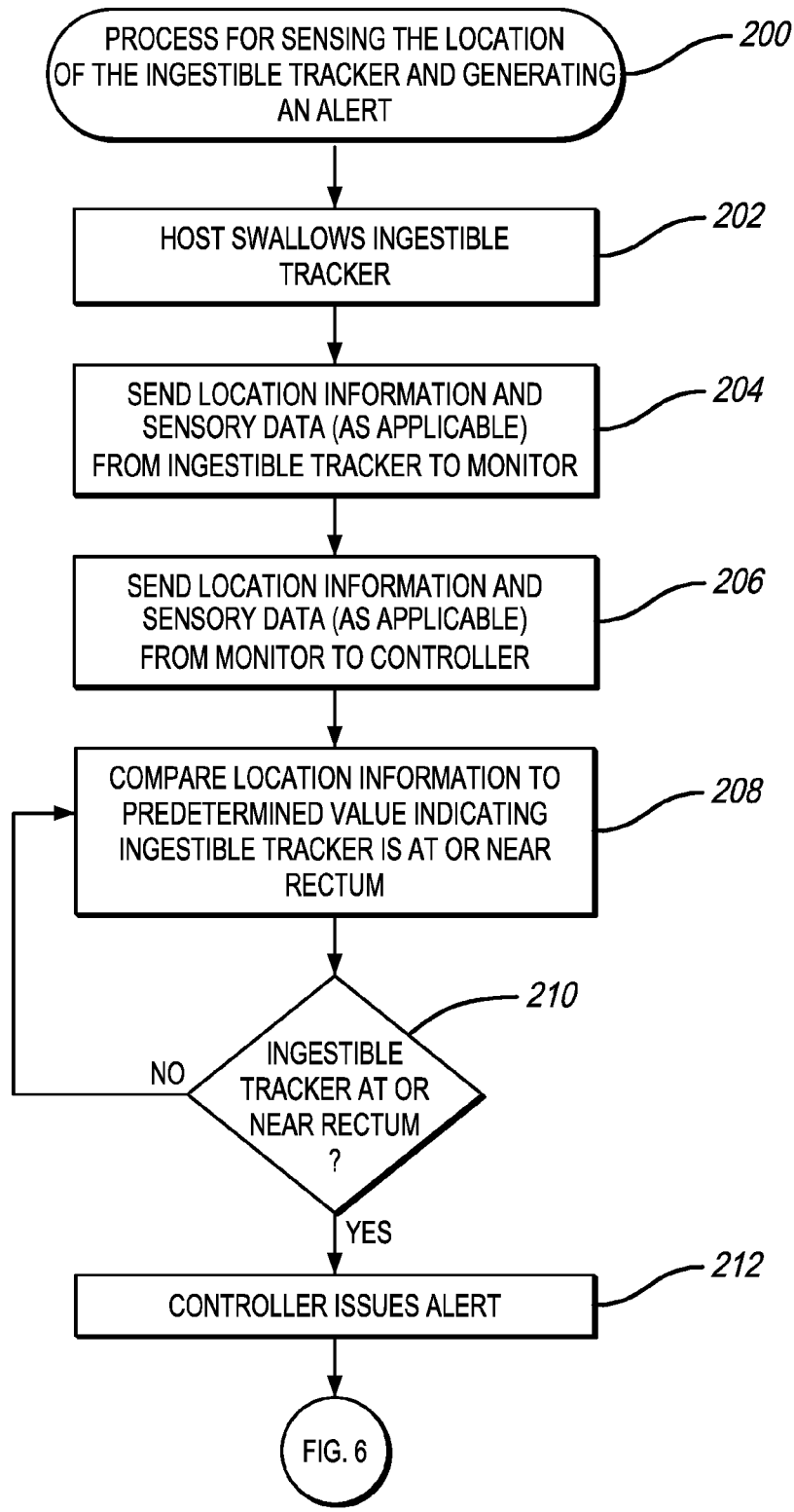
FIG. 5 is a flowchart illustrating a process for sensing the location of the ingestible tracker and generating an alert.
Figure 7:
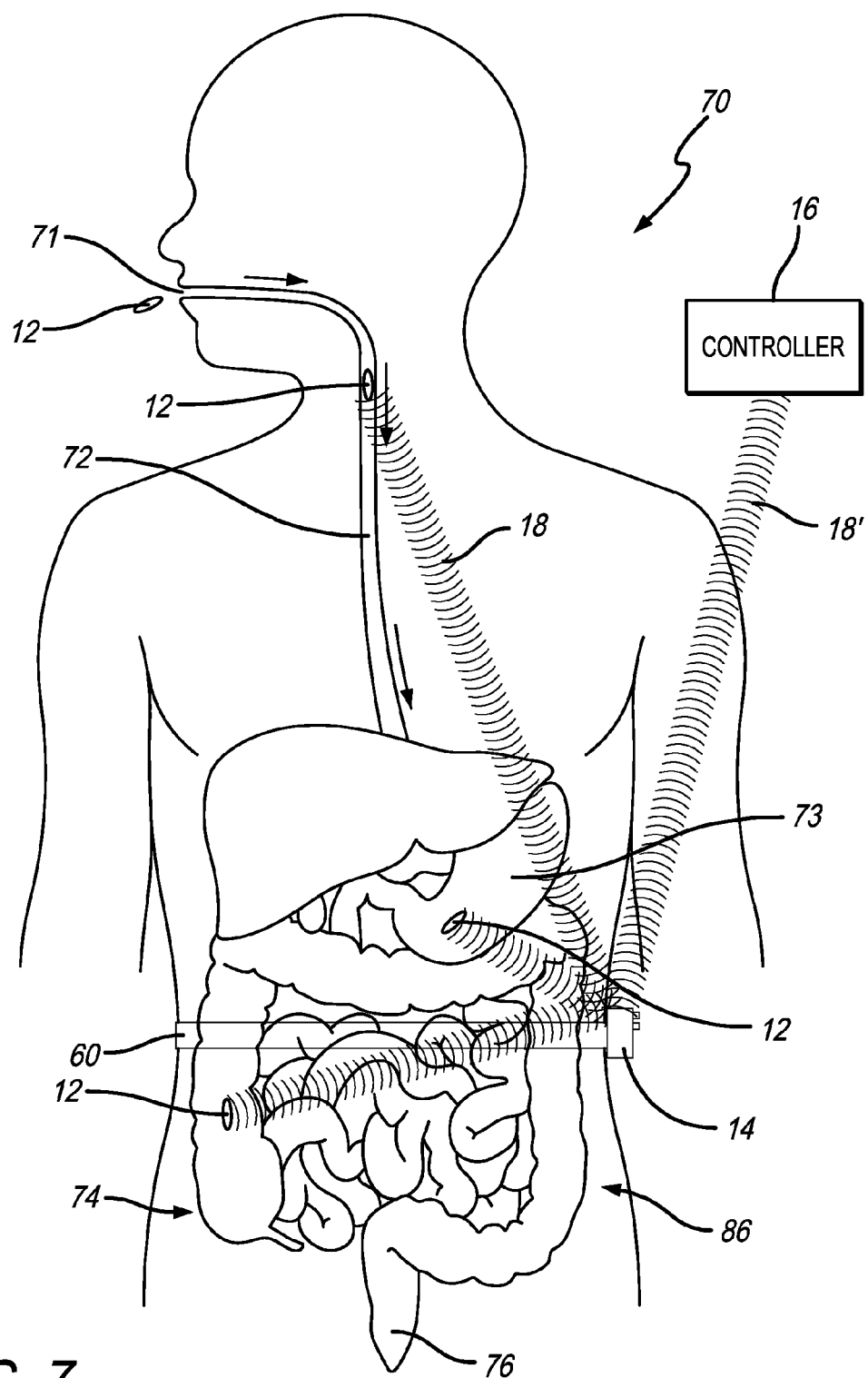
FIG. 7 is a diagrammatic view of the human host, more specifically illustrating ingestion and tracking of the ingestible tracker throughout a digestive tract.

FIG. 5 is a flowchart illustrating a process by which the defecation alert and control system 10 senses the location of the ingestible tracker 12 and issues a corresponding alert (200) to indicate an impending defecation. The first step (202) is for the host to swallow the ingestible tracker 12. In the embodiment related to the human host 70, this may be accomplished simply by swallowing the ingestible tracker 12 through the open mouth 71, as shown in FIG. 7. The ingestible tracker 12 then travels through the esophagus 72 on its way to the stomach 73 and the intestines 74. The wireless transmitter 46 within the ingestible tracker 12 may be activated prior to being swallowed or at some point thereafter, as mentioned above. For example, FIG. 7 illustrates the wireless signal 18 initially emanating from the ingestible tracker 12 when travelling through the esophagus 72. Alternatively, the wireless transmitter 46 may not activate until later on, such as after being triggered by a biological condition (e.g., within the stomach 73 or the intestines 74). This may occur, for example, once the dissolvable housing 50 of the outer casing 42 is dissolved in the stomach 73 or the intestines 74. Once activated, the ingestible tracker 12 may send location information and sensory data (as applicable) to the monitor 14 via the wireless signal 18 as part of step (204), and continuously thereafter as the ingestible tracker 12 moves through the host.

The body-mounted monitor 14 may then send the location information and sensory data (as applicable) to the controller 16 by way of the wireless signal 18' as part of step (206). Next, as part of step (208), the controller 16 compares the location information received from the monitor 14 to a predetermined value indicating whether the ingestible tracker 12 is at or near the rectum 76. In this respect, the next step (210) is to determine whether the ingestible tracker 12 is within the rectum 76. In the event the ingestible tracker 12 is not within the rectum 76, the controller 16 again compares the next set of location information to the predetermined value indicating the ingestible tracker 12 is at or near the rectum 76, as part of repeating step (208). Alternatively, once the controller 16 determines that the ingestible tracker 12 is at or near the rectum 76 (e.g., when the location information received by the controller 16 matches or falls within a certain range of the predetermined value), the controller 16 then issues an alert 80 as part of step (212), such as the one shown with respect to FIG. 8.

Figure 8:
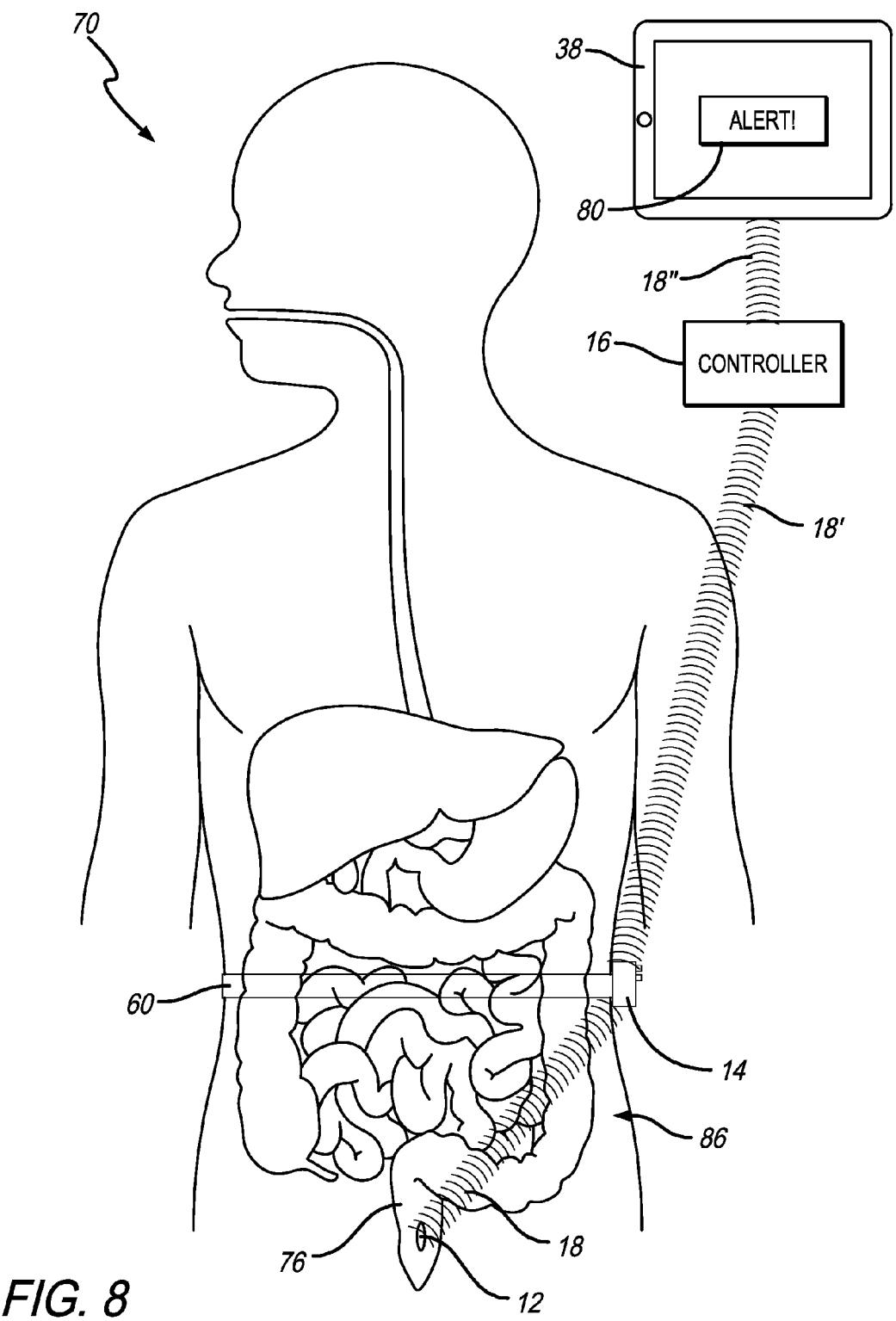
FIG. 8 is a diagrammatic view of the human host of FIG. 7, further illustrating activation of an alert when the ingestible tracker is at or near a rectum of the human host.

In this respect, FIG. 8 is a diagrammatic view similar to FIGS. 4 and 7, further illustrating wherein the system 10 determines, e.g., as part of step (210) in FIG. 5, that the ingestible tracker 12 is at or near the rectum 76 of the human host 70. As mentioned above, in one embodiment, the ingestible tracker 12 may generally send wireless signals 18 to the monitor 14 while traveling through the human host 70. When the ingestible tracker 12 arrives at or near the rectum 76, at least the location information received by the controller 16 by way of the wireless signals 18' from the wearable monitor 14 matches (or closely resembles) the predetermined value indicating that the ingestible tracker 12 is located at or near the rectum 76. In this respect, the controller 16 may directly issue the alert 80 as part of step (212). With respect to FIG. 8, the controller 16 is in wireless communication with the networked computer 38 and issues the alert 80 thereto by way of the wireless signal 18". The networked computer 38 may be any computer known in the art, such as a tablet (shown in FIG. 8), Smartphone, desktop or laptop computer, or other electronic notification device, such as an in-home security system. Furthermore, multiple networked computers 38 may be in communication with the controller 16 via the wireless signal 18" (e.g., a tablet, Smartphone, and in-home security system), all or a select group of which may receive and/or generate the alert 80 as part of step (212).

Figure 6:
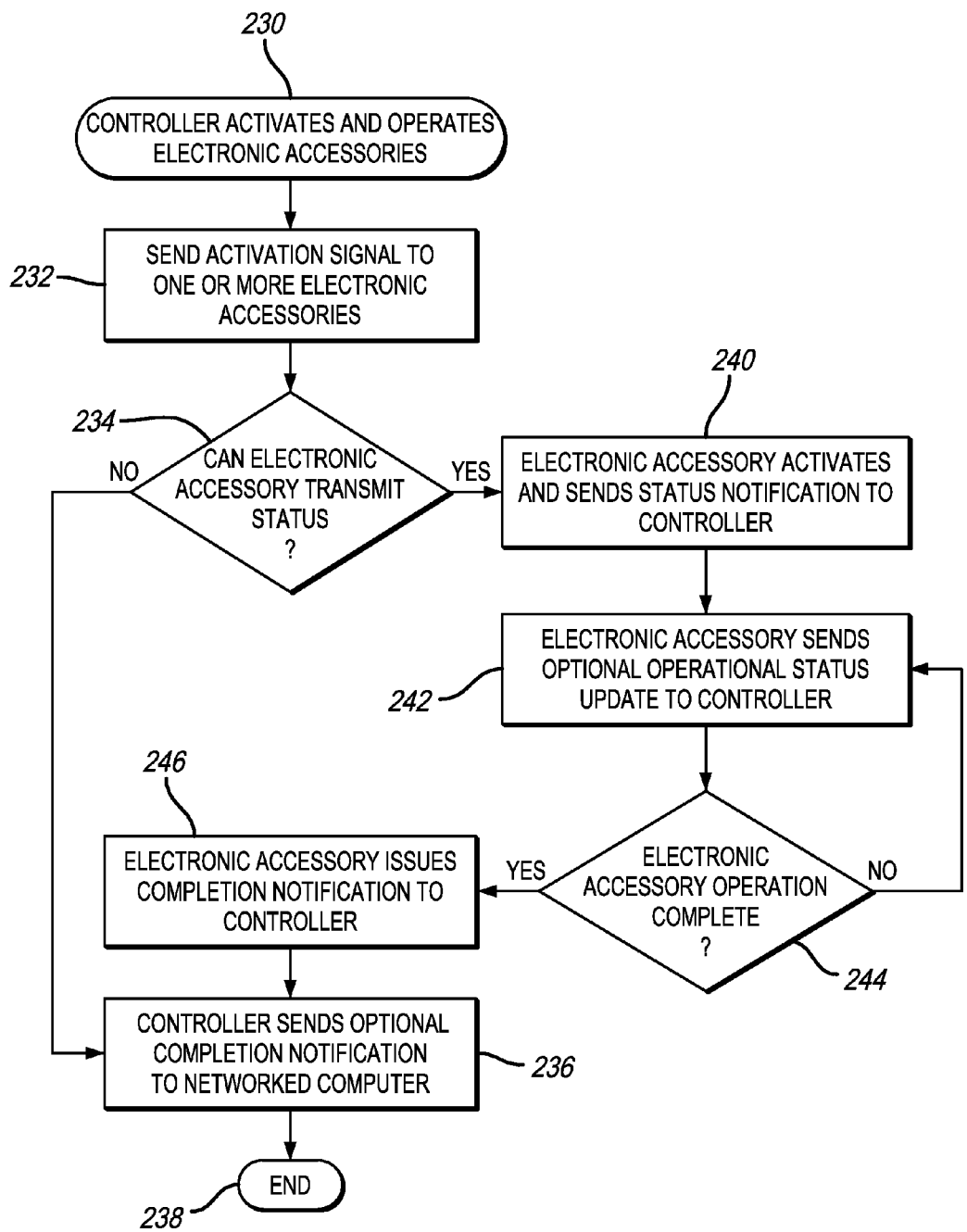
FIG. 6 is a flowchart further illustrating a process for activating and operating one or more of the electronic accessories.

After issuing the alert 80 as part of step (212), the system 10 may optionally proceed with the process (230) shown in FIG. 6, namely the controller 16 may activate and/or operate one or more of the electronic accessories 19. As such, the first step (232) in the process (230) shown with respect to FIG. 6 is to send an activation signal to one or more of the electronic accessories 19 in communication with the controller 16. The next step (234) is to determine whether each of the activated electronic accessories 19 can transmit its status. For any of the electronic accessories 19 that cannot communicate or transmit status information to the controller 16 (i.e., the electronic accessory may only receive unilateral communications from the controller 16), the controller 16 may send an optional completion notification to the networked computer 38 as part of process step (236) before ending the process (238). If any of the electronic accessories 19 are able to engage in bilateral communication with the controller 16, as determined as part of step (234), the next step (240) is for those electronic accessories 19 to activate and send a status notification back to the controller 16. Thereafter, these electronic accessories 19 may optionally continue to send operational updates to the controller 16 during the course of operation, as part of step (242). The next step (244) in the feedback cycle is to determine whether any of the electronic accessories 19 have completed operation. Those electronic accessories 19 that have not completed operation cycle back to step (242), and may provide another operational status update to the controller 16. In this respect, in the event that any of the electronic accessories 19 have completed operation as part of the determination step (244), such electronic accessories 19 may relay a completion notification (246) to the controller 16 and the process (230) may thereafter end (238).

Figure 9:
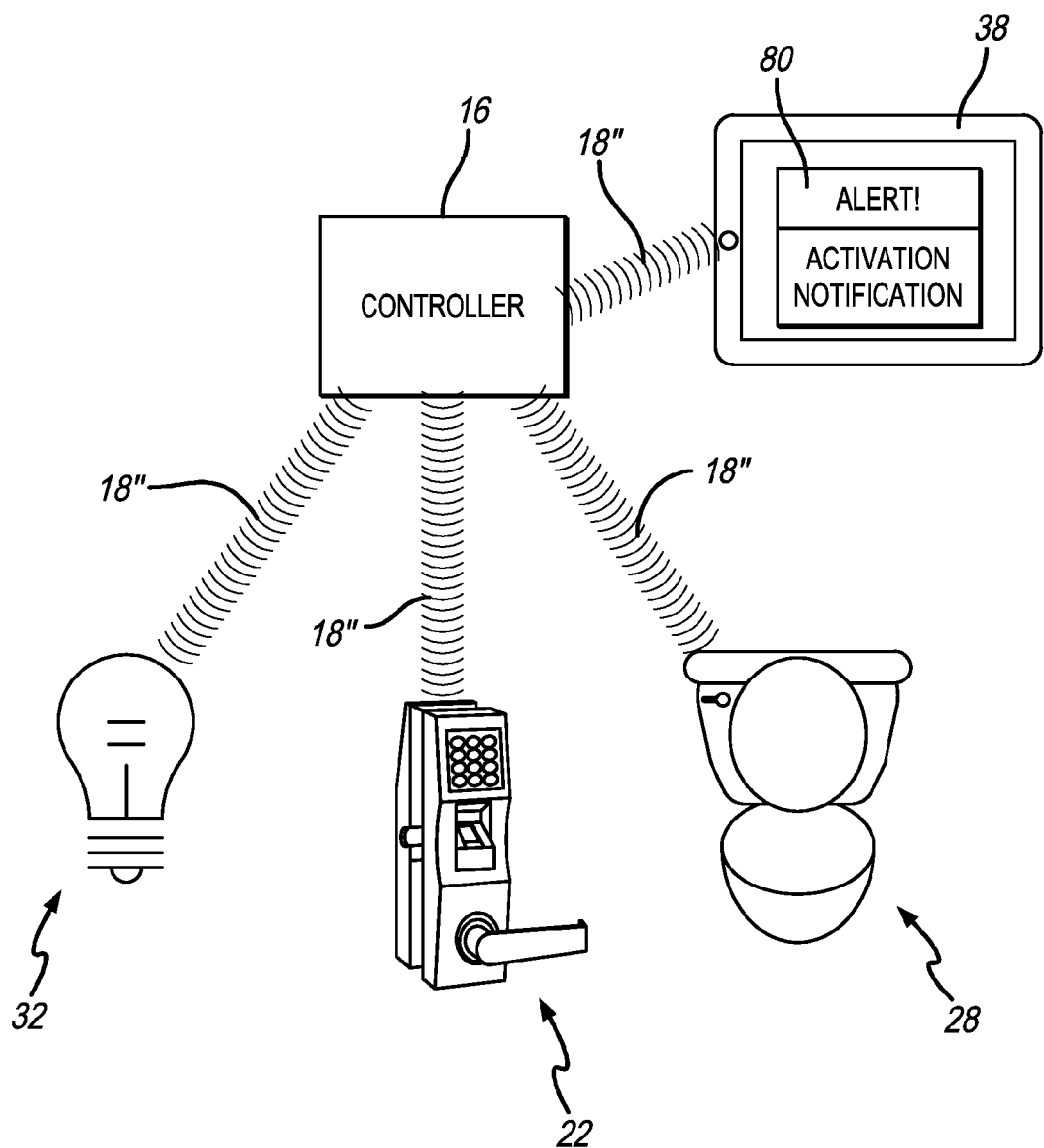
FIG. 9 is a diagrammatic view illustrating the controller sending a set of activation signals to an electronic door lock, an electrically-actuating toilet valve, and a lighting system after issuing an alert to a networked computer.

FIG. 9 illustrates an embodiment wherein the controller 16 is in communication with both the networked computer 38 and several electronic accessories, including the electronic door lock 22, the electrically-actuating toilet valve 28, and the lighting system 32. As described above, the controller 16 may issue the alert 80 to the networked computer 38 over the wireless signal 18" as part of step (212) in FIG. 5. Additionally, the controller 16 may also operate one or more of the electronic accessories 19 in accordance with the process for activating and/or operating the electronic accessories (230) shown with respect to FIG. 6. In FIG. 9, the controller 16 is shown sending communication information to each of the electronic door lock 22, the electrically-actuating toilet valve 28, and/or the lighting system 32 by way of the above-described respective wireless signals 18". The communication information may be sent in response to feedback information and/or conditions received and/or generated by the monitor 14 and/or the tracker 12. Here, as shown between FIGS. 9 and 10, the controller 16 may initiate wireless communications with each of the electronic door lock 22, the electrically-actuating toilet valve 28, and/or the lighting system 32 (FIG. 9), such as by way of the controller 16 sending the activation signal in step (232). Furthermore, each of the electronic door lock 22, the electrically-actuating toilet valve 28, and/or the lighting system 32 may then communicate back with the controller 16 (FIG. 10) over the respective wireless signals 18", such as by way of the electronic accessories sending a status notification to the controller 16 as part of activation step (240), sending optional status updates in step (242), or sending a completion notification in step (246).

Figure 10:
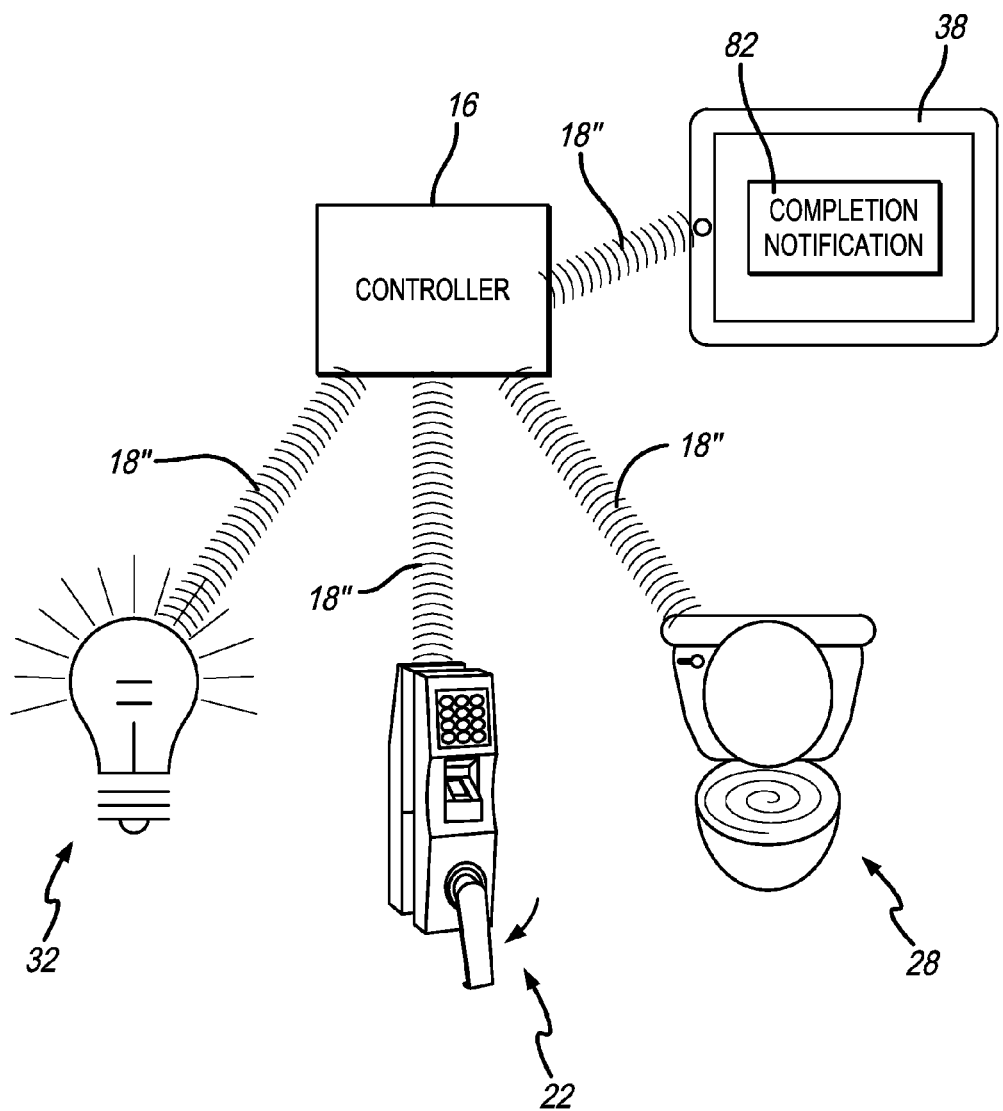
FIG. 10 is a diagrammatic view similar to FIG. 9, further illustrating the controller receiving wireless status updates from the electronic door lock, the electrically-actuating toilet valve, and the lighting system, and issuing a completion notification to the networked computer thereafter.
Figure 13A:
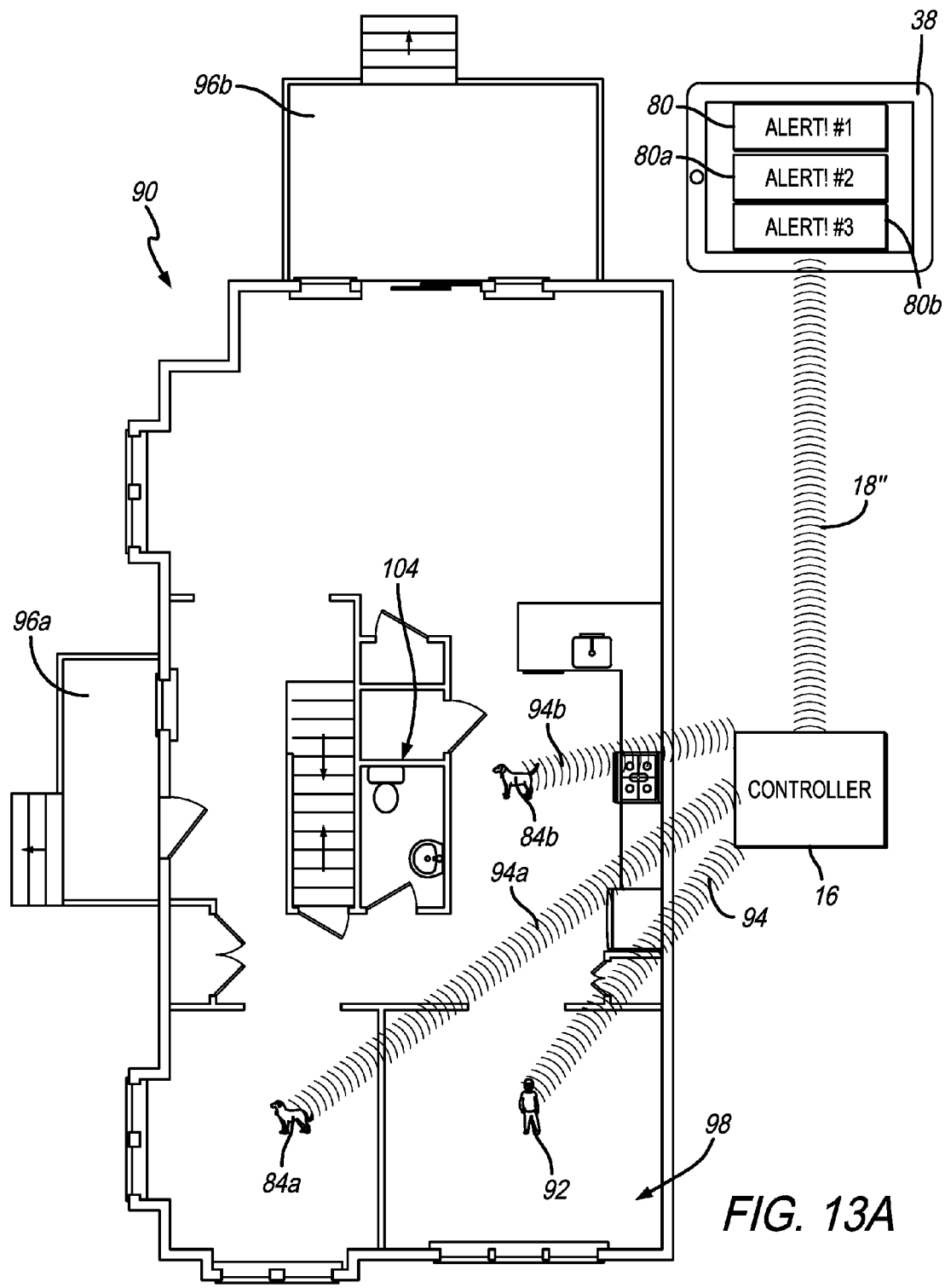
FIG. 13A is a diagrammatic view of a residential structure housing a pair of host dogs and a host child, wherein the controller receives data indicating that each host has an ingestible tracker at or near the rectum and issues an alert to a networked computer regarding the same.
Figure 13B:
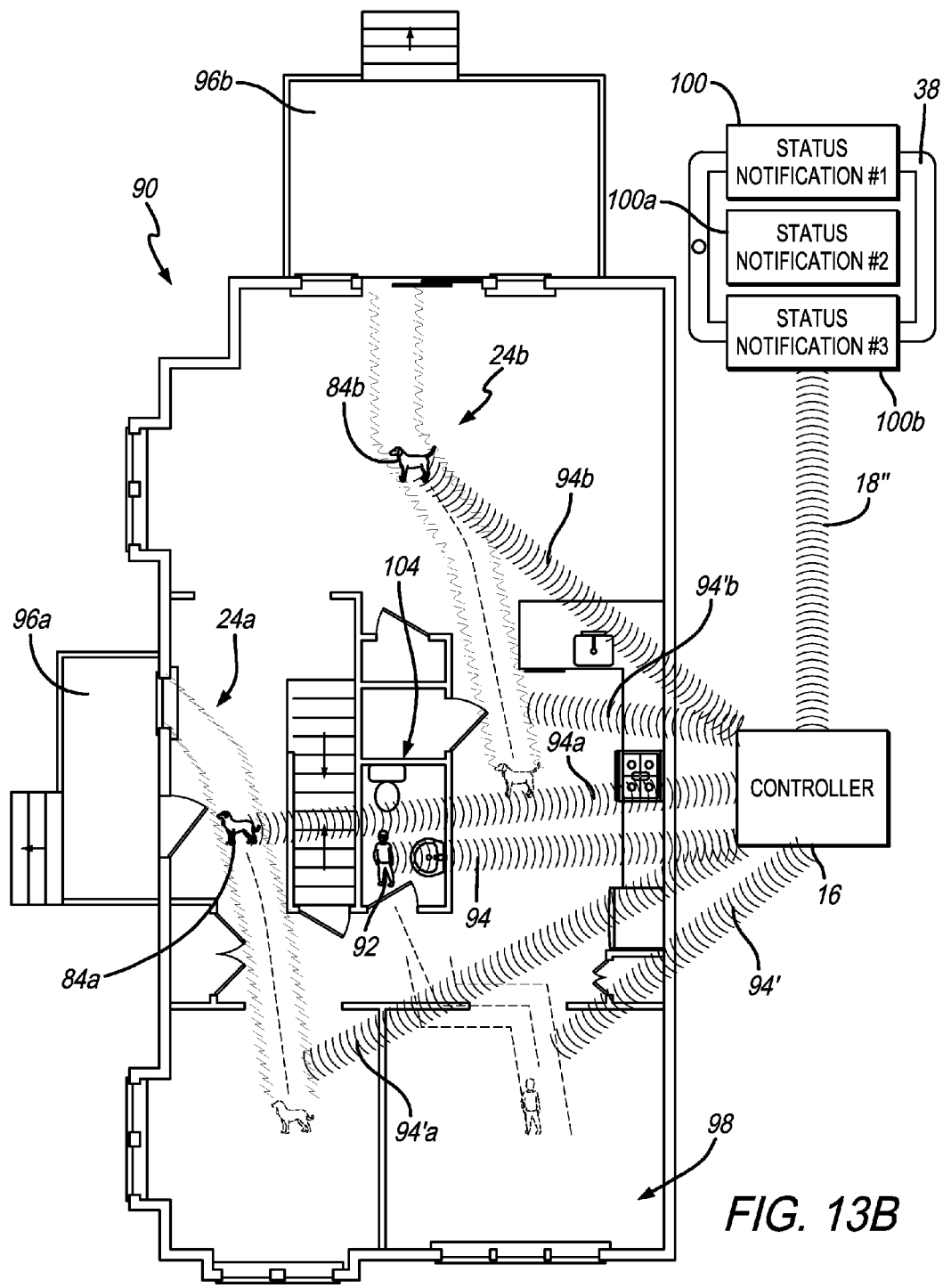
FIG. 13B is a diagrammatic view of the residential structure of FIG. 13A, further illustrating the controller activating two separate electric pathways for guiding each dog out of the house and a lighting system for guiding the child to a nearby restroom, and relaying status information to the networked computer regarding the same.

In one embodiment, the controller 16 may communicate directly with the lighting system 32 for automatic operation thereof. In some embodiments, the lighting system 32 may include a single light bulb (e.g., as shown in FIGS. 13A and 13B), multiple light bulbs, multiple lights within a particular room, building, or campus, or a lighted pathway, which may illuminate for purposes of directed guidance, as disclosed herein. Initially, the controller 16 sends a signal to the lighting system 32, which is "off" as shown in FIG. 9. In response to the wireless signal 18", the lighting system 32 may turn "on" as shown in FIG. 10. In the event the lighting system 32 includes a communication device (such as a wireless or wired data communication transmitter), the lighting system 32 may send a return signal to the controller 16 indicating that the lighting system 32 has been turned "on". The controller 16 may then send a completion notification 82 (FIG. 10) to the networked computer 38 by way of the wireless signal 18" to notify a user or operator that the lighting system 32 was, in fact, turned "on" in response to notification from the ingestible tracker 12 of an impending defecation. The system 10 can provide remote notifications to caretakers, for example, even though the caretaker may not be in the immediate location (or even on premises).

In a second example illustrated in FIGS. 9 and 10, the controller 16 may remotely operate the electronic door lock 22 in response to feedback from the monitor 14 (or the tracker 12), such as by way of relaying "unlock" instructions over the wireless signal 18". The electronic door lock 22 may electronically operate to move the handle from the locked position (FIG. 9) to an unlocked position (FIG. 10). Accordingly, once complete, the electronic door lock 22 may relay information back to the controller 16 to indicate that the electronic door lock 22 is now "unlocked". Here, the controller 16 can notify a caretaker that this step is complete (i.e., the electronic door lock 22 is, in fact, "unlocked"), such as by way of the completion notification 82 delivered to the networked computer 38. In this respect, the electronic door lock 22 may relate specifically to a single door lock (e.g., bathroom entrance), a plurality of door locks (e.g., hospital room door and hallway bathroom), etc.

In a third embodiment shown with respect to FIGS. 9 and 10, the controller 16 may also be in wireless communication with an electrically-actuating toilet valve 28. In this embodiment, the controller 16 may receive feedback from the monitor 14 (or the tracker 12) that the ingestible tracker 12 is no longer in the host, e.g., in the bowl of the toilet by way of a bowel movement. The monitor 14 or the tracker 12 may notify the controller 16 that the ingestible tracker 12 is no longer in the host, e.g., by way of sensing a relatively rapid descent from the rectum 76 or by way of a sensor in the toilet that identifies the presence or proximity of the ingestible tracker 12 therein. Thereafter, the controller 16 may send an activation signal by way of the wireless signal 18" to operate the electrically-actuating toilet valve 28, thereby "flushing" the toilet. Once the toilet has been "flushed", a signal may be returned to the controller 16 indicating as such, so the controller 16 can then provide the completion notification 82 to the networked computer 38. Such a feature may be advantageous, e.g., in a hospital environment, so caretakers (e.g., nurses or parents) know when the cared for person has gone to the bathroom.

Figure 11:
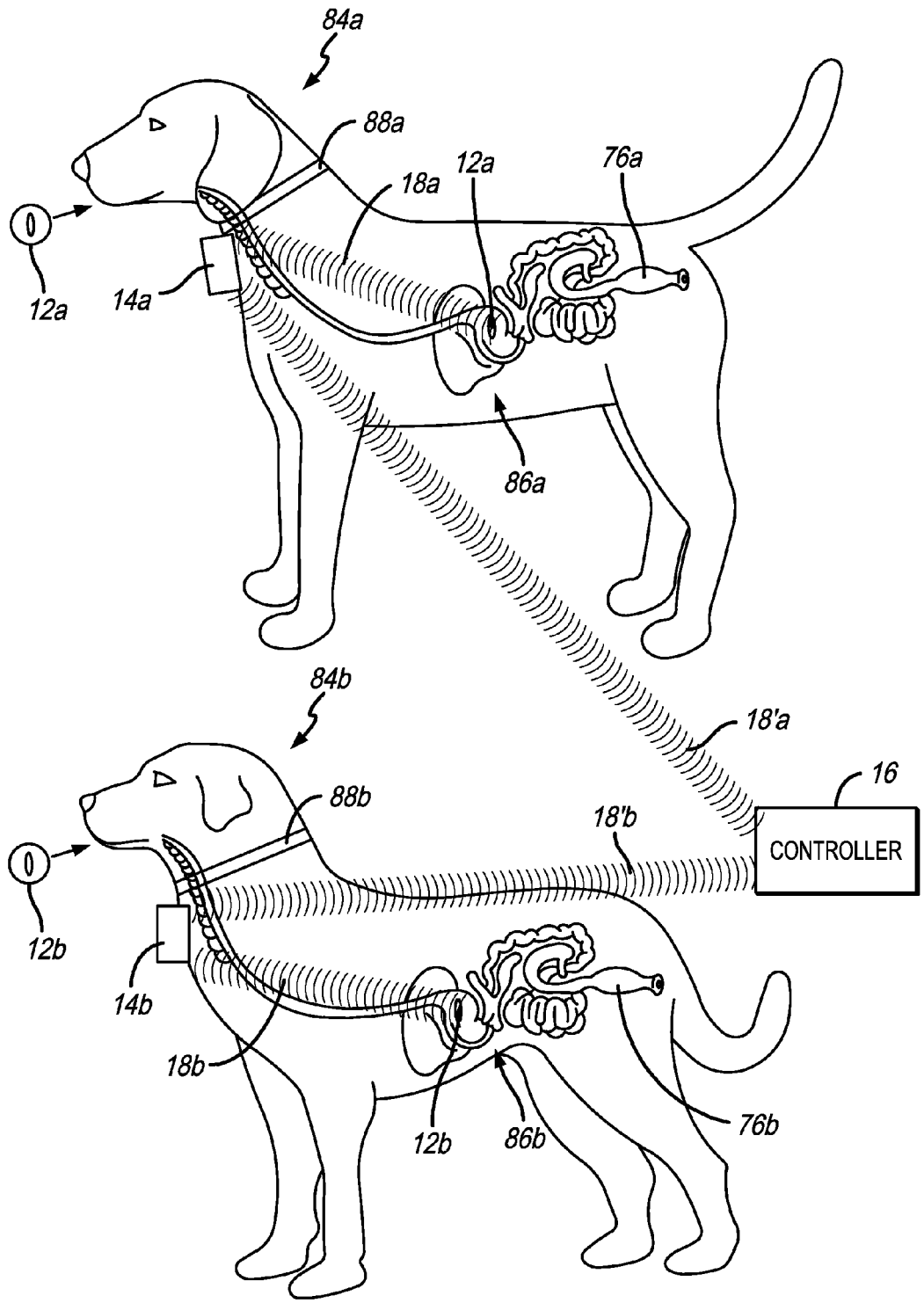
FIG. 11 is a diagrammatic view of a pair of host dogs each having an ingestible tracker in their digestive track and simultaneously communicating with the controller.
Figure 12:
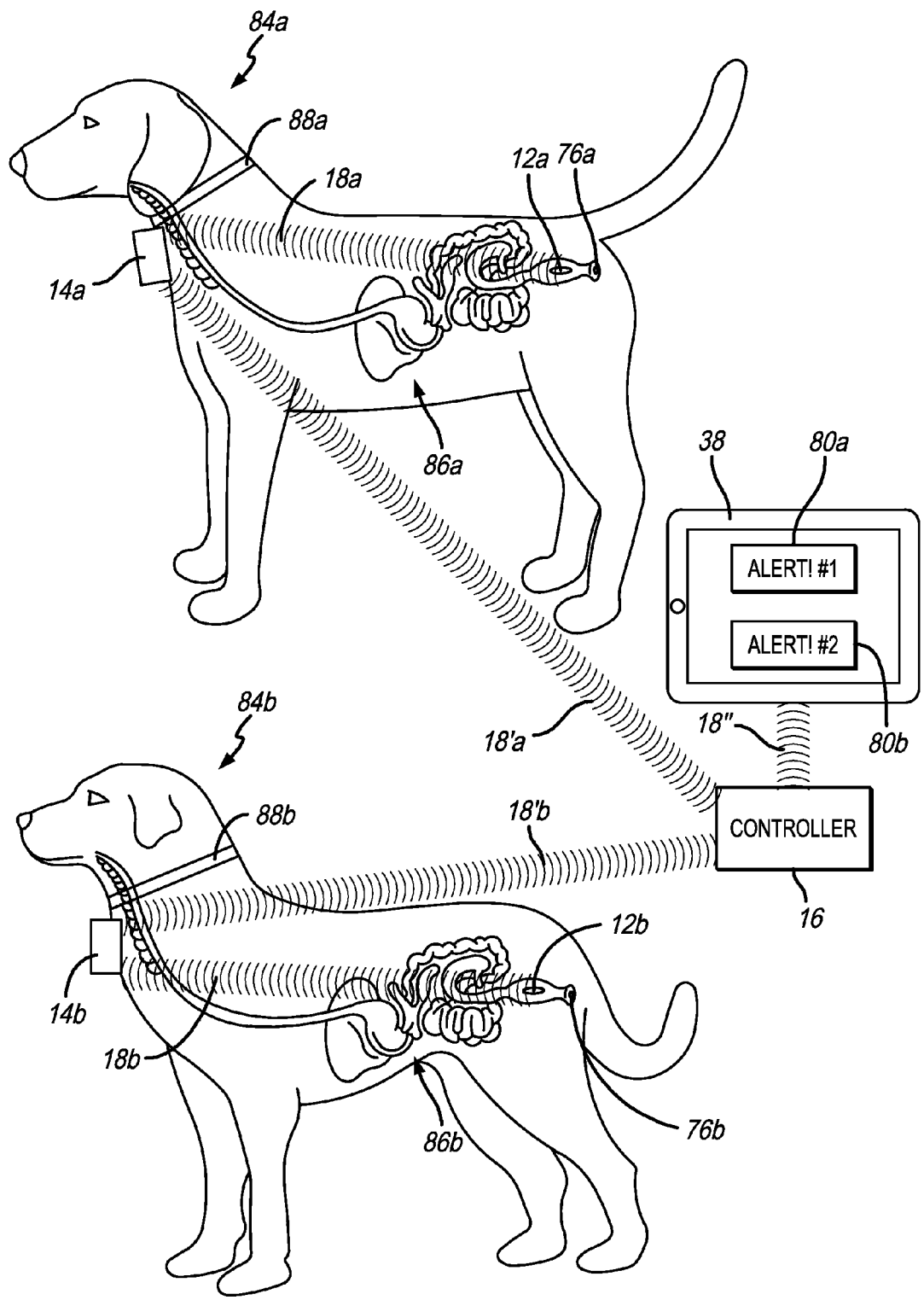
FIG. 12 is a diagrammatic view similar to FIG. 11, further illustrating the controller issuing two unique alerts to a networked computer, indicating that each respective ingestible tracker reached the rectum of each of the host dogs.

In another aspect of the defecation alert and control system 10 disclosed herein, FIGS. 11 and 12 illustrate multiple ingestible trackers 12a, 12b in concurrent use in association with a pair of dogs 84a, 84b. More specifically, FIG. 11 illustrates each of the dogs 84a, 84b swallowing respective ingestible trackers 12a, 12b for travel through respective digestive tracts 86a, 86b, similar to the embodiments disclosed above with respect to the human host 70 and movement of the ingestible tracker 12 through the open mouth 71, the esophagus 72, the stomach 73, the intestines 74, and finally the rectum 76. In one embodiment, the ingestible trackers 12a, 12b may be intermixed with dog food such that the dogs 84a, 84b unknowingly ingest the trackers 12a, 12b as part of routine meals. Once swallowed, each of the ingestible trackers 12a, 12b may communicate with a pair of respective monitors 14a, 14b that report to the common controller 16. The monitors 14a, 14b may be attached to each of the dogs 84a, 84b by a pair of respective collars 88a, 88b, similar to the belt 60 described above with respect to the human host 70. In this embodiment, the monitors 14a, 14b may remain a relatively fixed distance from the respective rectums 76a, 76b for purposes of determining the location of the ingestible trackers 12a, 12b within the respective dogs 84a, 84b. Additionally, the collars 88a or 88b may incorporate electronics to provide stimuli (e.g., mild electric current) to one or more of the dogs 84a, 84b.

During the course of travel through the respective digestive tracts 86a, 86b, each of the ingestible trackers 12a, 12b may periodically send location information and/or other biological data (as needed and/or desired) via distinct wireless signals 18a, 18b to the corresponding monitors 14a, 14b. Each of the monitors 14a, 14b may then send the location information and/or other biological data (as needed and/or desired) to the controller 16 via the wireless signals 18'a, 18'b for comparative analysis as described herein. In an alternative embodiment, as described above, the ingestible trackers 12a, 12b may not activate and transmit the wireless signals 18a, 18b until after a triggering event, such as after digesting the dissolvable housing 50. The monitors 14a, 14b, regardless whether they continue to track the location of the ingestible trackers 12a, 12b throughout the respective digestive tracts 86a, 86b, may identify when the respective ingestible trackers 12a, 12b reach the respective rectums 76a, 76b, thus indicating that one or both of the dogs 84a, 84b need(s) to defecate.

In this respect, FIG. 12 more specifically illustrates the positioning of the ingestible trackers 12a, 12b in each target destination within the respective rectums 76a, 76b of each of the dogs 84a, 84b. Of course, it may be possible that the ingestible trackers 12a, 12b reach the respective rectums 76a, 76b at different times. That is, the ingestible tracker 12a corresponding with the dog 84a may reach the rectum 76a in the morning, while the ingestible tracker 12b of the dog 84b may reach the rectum 76b in the afternoon or in the evening. Alternatively, the ingestible trackers 12a, 12b may reach the respective rectums 76a, 76b at about the same time. Regardless, each of the monitors 14a, 14b emit unique wireless signals 18'a, 18'b so that the controller 16 can specifically identify which of the dogs 84a, 84b may need to defecate at any given time. In this respect, the controller 16 compares the data received from each respective monitor 14a, 14b to predetermined (possibly unique) values for each of the dogs 84a, 84b. As an example, in FIG. 12, since the ingestible trackers 12a, 12b have reached the respective rectums 76a, 76b, the controller 16 recognizes the match in comparison data for each of the dogs 84a, 84b, and the controller 16 issues a pair of respective alerts 80a, 80b to the networked computer 38 over the wireless signal 18", corresponding with each of the dogs 84a, 84b. This way, the owner of the dogs 84a, 84b, for example, may be notified that one or both need to defecate.

Figure 13C:
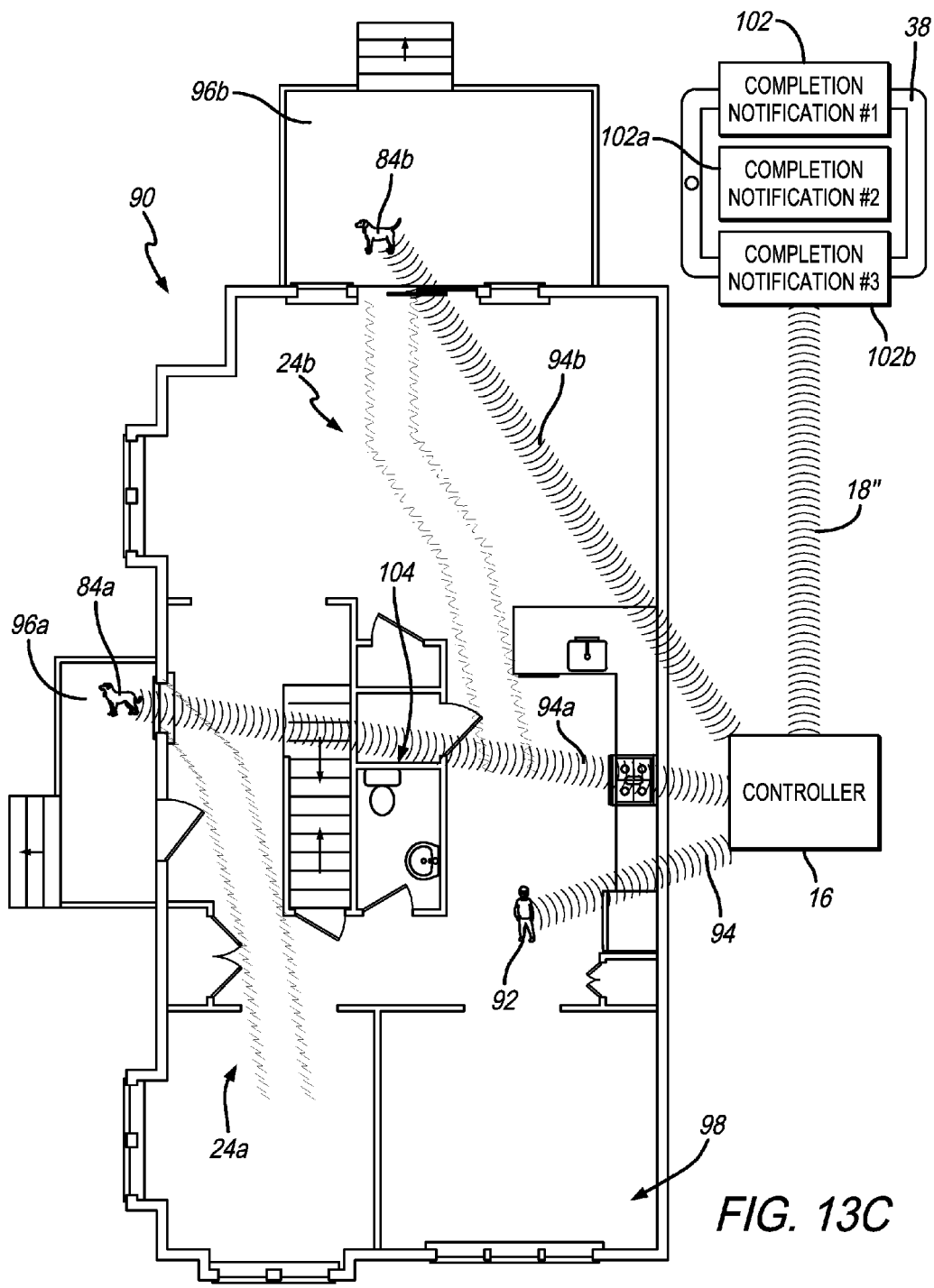
FIG. 13C is a diagrammatic view of the residential structure of FIGS. 13A and 13B, further illustrating the controller receiving data indicating that each of the host dogs and the host child defecated, and issuing a completion notification to the networked computer regarding the same.

FIGS. 13A-13C are top-down diagrammatic views illustrating implementation of the defecation alert and control system 10 in a residential structure 90, and specifically with respect to the pair of dogs 84a, 84b and a child 92. In this respect, in general, FIG. 13A illustrates the controller 16 receiving notification that each of the pair of dogs 84a, 84b and/or the child 92 need to defecate, such as by way of the respective uniquely identifiable wireless signals 94, 94a, 94b. The controller 16 then sends a trio of alerts 80, 80a, 80b to the networked computer 38 over the wireless signal 18" for user notification (e.g., on a tablet, Smartphone, or the like). Next, the controller 16 may send one or more operational instructions directly to one or more of the electronic accessories 19 integrated with the system 10, such as over a set of uniquely identifiable wireless signals 94', 94'a, 94'b shown with respect to FIG. 13B, in response to the indication that one or more of the dogs 84a, 84b and/or the child 92 needs to defecate.

Specifically with respect to the dogs 84a, 84b, the controller 16 may activate an electronic pathway 24a designed to guide the dog 84a to an outside area 96a where the dog 84a can defecate. In this respect, the controller 16 is able to specifically activate the electronic pathway 24a based on the unique wireless signal 94'a. Similarly, the controller 16 may activate an electronic pathway 24b designed to guide the dog 84b to an outside area 96b where the dog 84b can defecate. The controller 16 is able to specifically activate the electronic pathway 24b based on the unique wireless signal 94'b, which may be different than the wireless signal 94'a generated with respect to the dog 84a. In each instance, activation of a corresponding training collar 26 (e.g., integrated into the collars 88a, 88b) worn by the dogs 84a, 84b may further help guide the dogs 84a, 84b to the respective outside areas 96a, 96b. Moreover, one or both of the outside areas 96a, 96b may include an optional defecation mat (e.g., illuminated or non-illuminated) to signal a location in one or more of the outside areas 96a, 96b appropriate for defecation.

In this respect, FIG. 13B further illustrates each of the dogs 84a, 84b moving along each of the respective electric pathways 24a, 24b toward the outside areas 96a, 96b. As part of this process, the controller 16 may provide a status notification 100a, 100b to the user by way of the networked computer 38 regarding the location and progress of each of the dogs 84a, 84b. FIG. 13C then shows that each of the dogs 84a, 84b have arrived at their intended destinations in each of the respective outside areas 96a, 96b where the dogs 84a, 84b may defecate. Thereafter, the controller 16 may relay a completion notification 102a, 102b to the networked computer 38 indicating such arrival or that one or both of the dogs 84a, 84b have defecated (e.g., when one or both of the respective ingestible trackers 12a, 12b have been passed out of the rectums 76a, 76b). The controller 16 may be able to identify this state by way of bilateral communication with one or more of the electronic accessories 19 over the wireless signals 94a, 94b or 94'a, 94'b, as described herein.

In general, the electric pathways 24a, 24b may act as an electric fence to train the dogs 84a, 84b to follow a specific path to the outside areas 96a, 96b for purposes of defecating. In this respect, the controller 16 is able to specifically activate one or both of the electronic pathways 24a, 24b based on the uniquely identifiable wireless signals 94a, 94b and/or 94'a, 94'b. Alternatively, the controller 16 may also be able to identify the specific location of the dogs 84a, 84b within the residential structure 90, and activate the closest corresponding or most efficient electric pathway 24a or 24b to facilitate access to the outside areas 96a or 96b. The controller 16 may also activate one or both of the electric pathways 24a, 24b, depending on the location and whether one or both of the dogs 84a, 84b need to defecate.

In another embodiment, FIG. 13A illustrates the child 92 within a bedroom 98 in a state wherein the controller 16 identifies that the child 92 needs to defecate. Here, as briefly mentioned above, the controller 16 may first issue the alert 80 to the networked computer 38. Then, as shown in FIG. 13B, the controller 16 may send the wireless signal 94' to activate the lighting system 32. The lighting system 32 may be a series of lights placed along or otherwise integrated into the floor to help guide the child 92 into a particular bathroom 104 in the event of a pending defecation. The lighting system 32 may include a plurality of LED lights integrated into the floor of the residential structure 90 such that the controller 16 may activate and/or deactivate certain lights to ensure the pathway directs the child 92 to the bathroom 104 based on the location of the child 92 when the controller 16 receives notification that the child 92 needs to defecate. Alternatively, the lighting system 32 may include a ceiling or wall-mounted projector that casts the lighted pathway onto the floor of the residential structure 90 to similarly guide the child 92 to a bathroom 104. In this respect, the lighting system 32 provides a visual indication to the child 92 of the need to defecate, and the lighting system 32 provides a lighted path to the bathroom 104. Once the child 92 reaches the bathroom 104, the controller 16 may send a signal to the electronic door lock 22 to open the bathroom 104, as described above with respect to FIGS. 9 and 10. Once inside, the controller 16 may relay a status notification 100 back to the networked computer 38 indicating that the child 92 is within the bathroom 104. Thereafter, the controller 16 may deactivate the lighting system 32, as shown between FIGS. 13B and 13C. Alternatively, the lighting system 32 shown in FIGS. 13A and 13B may remain active even after the child 92 enters the bathroom 104. In this respect, the lighting system 32 may remain "on" until the child 92 successfully defecates. The controller 16 may receive notification of such a successful defecation by way of a sensor in the toilet bowl. In this embodiment, the controller 16 may be able to determine when to activate the electrically-actuating toilet valve 28 to flush the toilet, as shown and described with respect to FIGS. 9 and 10 above. In another alternative embodiment, a third party caretaker may deactivate the lighting system 32 remotely through use of the networked computer 38.

Once complete, the controller 16 may relay a completion notification 102 to the networked computer 38 so the third party caretaker is aware the child 92 defecated and is no longer in the bathroom 104, as shown in FIG. 13C. Once the child 92 is no longer in the bathroom 104, the controller 16 may reactivate the electronic door lock 22 to lock the door to the bathroom 104.

The system 10 in FIGS. 13A-13C provides two automatic training responses for the child 92. First, identifying that the ingestible tracker 12 is at or near the rectum 76 of the child 92 allows the system 10 to visually provide notification to the child 92 of the need to defecate by way of the lighting system 32. This visual stimulation allows an untrained child 92 to correlate when it is time to go to the bathroom 104. Second, the lighting system 32 helps guide the child 92 to the bathroom 104. So, not only does the child 92 understand the need to defecate, but also that the bathroom 104 is the proper location for the defecation.

Following activation and/or deactivation of one or more of the electric pathways 24a, 24b and/or the lighting system 32 (or other electronic accessories as the case may be), the controller 16 may relay one or more completion notifications 102, 102a, 102b to the networked computer 38 to inform a third party caretaker or the like that the electronic accessories have completed operation within the residential structure 90. This third party caretaker may receive local or remote notification regarding when the dogs 84a, 84b and/or the child 92 needs to defecate, or has already defecated, by way of periodic status updates after receiving the first alert 80 and before receiving the completion notification 102, such as by way of step (240) as described above.

Moreover, the ingestible trackers 12, 12a, 12b may include one or more of the sensors 52 designed specifically to monitor and/or track movement of the host (e.g., the dogs 84a, 84b and/or the child 92). For example, the ingestible trackers 12, 12a, 12b within each of the dogs 84a, 84b and/or the child 92 shown with respect to FIGS. 13A-13C may include one or more of the sensors 52 capable of detecting or otherwise relaying location information to identify and/or help pinpoint the location of any one of the dogs 84a, 84b and/or the child 92 within the residential structure 90 (e.g., in real-time). Accordingly, the ingestible trackers 12, 12a, 12b may work in concert with other features, such as the video system 20 (e.g., to remotely view the dogs 84a, 84b and/or child 92), the electric pathways 24a, 24b, and/or the training collars 26a, 26b (e.g., to help guide movement of the dogs 84a, 84b).

In another alternative embodiment, when the controller 16 determines that one of the ingestible trackers 12a, 12b was released from one of the dogs 84a, 84b, such as by way of defecation in the outside area 96a, 96b, the controller 16 may relay a signal (e.g., wirelessly or by hardwire connection) to a food and/or water dispenser to provide more food for the dog 84a or 84b that defecated the ingestible tracker 12a or 12b. Here, the food and/or water dispenser may dispense a serving size of dog food and/or water for consumption by one or more of the dogs 84a or 84b. As such, the serving size of dog food may further include another ingestible tracker 12 such that, once ingested, the tracking starts over again.

Although several embodiments have been described in detail for purposes of illustration, various modifications may be made without departing from the scope and spirit of the invention. Accordingly, the invention is not to be limited, except as by the appended claims.

What is claimed is:

1. A process carried out with respect to a defecation control system, the process comprising the steps of:
   activating a communication circuit of at least one ingestible tracker having a size and shape for ingestion and travel to a rectum of a host and a transmission circuit of a monitor fixable to the host at a substantially constant distance relative to the rectum;
   generating at least one tracking distance based at least in part on communication between the communication circuit of the ingestible tracker and the transmission circuit of the monitor;
   comparing the tracking distance to a predetermined trigger distance stored in a database; and
   operating an electronic accessory when the tracking distance is within a predetermined threshold of the trigger distance indicating the host needs to defecate.

2. The process of claim 1, wherein the generating step includes the step of calculating the at least one tracking distance based on the positioning of the ingestible tracker relative to the monitor.

3. The process of claim 1, wherein the electronic accessory comprises a camera and the operating step includes the step of recording at least one picture of the host with the camera and relaying the at least one picture for remote viewing.

4. The process of claim 1, wherein the electronic accessory comprises a door lock and the operating step includes the step of unlocking the door lock.

5. The process of claim 1, wherein the electronic accessory comprises an audio system and the operating step includes the step of initiating an audible alarm.

6. The process of claim 1, wherein the electronic accessory comprises a networked computer and the operating step includes the step of issuing an alert to the networked computer.

7. The process of claim 1, wherein the generating step includes the step of generating multiple tracking distances at different times for real-time comparison to the predetermined trigger distance.

8. The process of claim 1, wherein the operating step includes the step of changing the electronic accessory from a first non-use state to a second use state, and issuing an operation notification when the electronic accessory is in the second use state.

9. The process of claim 8, wherein the changing step further includes changing the electronic accessory back from the second use state to the first non-use state and issuing a completion notification.

10. The process of claim 1, further including the step of simultaneously tracking the location of multiple ingestible trackers each having unique and varying real-time tracking distances for simultaneous comparison with respective unique and predetermined trigger distances.

11. The process of claim 1, wherein the generating step includes the step of the transmission circuit sending a transmission query to the communication circuit comprising a passive RFID circuit, and energizing the RFID circuit with the transmission query whereby the RFID circuit provides a response.

12. A defecation alert system, comprising:
   an ingestible tracker having a size and shape for ingestion and travel to a rectum of a host and including a communication circuit;
   a monitor fixable to the host at a substantially constant distance relative to the rectum and having a transmission circuit for communication with the communication circuit of the ingestible tracker, wherein communication between the communication circuit and the transmission circuit establishes at least one tracking distance the ingestible tracker is from the rectum of the host;
   a controller including a network adapter that can communicate with the monitor and/or the ingestible tracker to at least receive the at least one tracking distance for comparison to a trigger distance stored in a database, wherein when the tracking distance is within a predetermined threshold of the trigger distance, the controller can identify that the host needs to defecate; and
   an electronic accessory configured to at least receive operational instructions from the controller, wherein the controller can issue at least one operational instruction to change the electronic accessory from a first non-use state before the controller identifies that the host needs to defecate to a second use state after the controller identifies that the host needs to defecate.

13. The defecation alert system of claim 12, wherein the electronic accessory comprises a networked computer and the second use state comprises an alert.

14. The defecation alert system of claim 12, wherein the communication circuit comprises an RFID chip, a Bluetooth transmitter, or an RSSI circuit.

15. The defecation alert system of claim 14, wherein the RFID chip comprises a passive RFID circuit.

16. The defecation alert system of claim 15, wherein the transmission circuit includes a reader for querying the passive RFID circuit.

17. The defecation alert system of claim 12, wherein the communication circuit, the transmission circuit, and the network adapter communicate wirelessly.

18. The defecation alert system of claim 12, wherein the ingestible tracker includes an outer casing hermetically sealing the communication circuit therein.

19. The defecation alert system of claim 18, wherein at least a portion of the outer casing includes a dissolvable housing that exposes at least one sensor once dissolved.

20. The defecation alert system of claim 19, wherein the communication circuit remains hermetically sealed within the outer casing after the dissolvable housing dissolves to expose the sensor.

21. The defecation alert system of claim 18, wherein the outer casing comprises metal, ceramic, or a polymer.

22. The defecation alert system of claim 12, wherein the monitor includes a clip for attachment to an article of clothing.

23. The defecation alert system of claim 12, wherein the electronic accessory comprises a video system, an electronic door lock, an electronic pathway, a training collar, an electrically-actuating toilet valve, a siren, a lighting system, an audio replay system, or a food dispenser.

24. A process carried out with respect to a defecation control system, the process comprising the steps of:
    activating a communication circuit of an ingestible tracker having a size and shape for ingestion and travel to a rectum of a host;
    capturing at least one image within a tractus digestorius of the host with a camera associated with the ingestible tracker;
    analyzing the at least one image for biological characteristics;
    comparing the biological characteristics to trigger characteristics; and
    operating an electronic accessory when the biological characteristics are within a predetermined percentage of the trigger characteristics indicating the ingestible tracker is in a location at or near the rectum such that the host needs to defecate.

25. The process of claim 24, wherein the operating step includes the step of energizing the electronic accessory comprising an electronic fence leading the host to a designated defecation area and operable with a wearable shock collar.

26. The process of claim 24, wherein the electronic accessory comprises a toilet and the operating step includes the step of actuating a flush valve.

27. The process of claim 24, wherein the activating step includes the step of activating the communication circuit of the ingestible tracker after dissolving at least part of a housing of the ingestible tracker to expose the camera.

28. The process of claim 24, wherein the electronic accessory comprises a lighting system and the operating step comprises illuminating a path to a bathroom.

29. The process of claim 24, further including the step of sensing removal of the ingestible tracker from the host and issuing a removal notification.

30. The process of claim 29, further including the step of dispensing consumables in response to sensed removal of the ingestible tracker from the host.

* * * * *